(12) United States Patent
Grant et al.

(10) Patent No.: US 10,969,609 B2
(45) Date of Patent: Apr. 6, 2021

(54) CONTACT LENS USE IN THE TREATMENT OF AN OPHTHALMOLOGIC CONDITION

(71) Applicant: Osio Corporation, Coronado, CA (US)

(72) Inventors: Stuart C. Grant, Los Angeles, CA (US); Alberto Osio Hernandez-Pons, Mexico City (MX); John Michael Rinehart, Peoria, AZ (US)

(73) Assignee: Osio Corporation, Coronado, CA (US)

( * ) Notice: Subject to any disclaimer, the term of this patent is extended or adjusted under 35 U.S.C. 154(b) by 0 days.

(21) Appl. No.: 16/378,457

(22) Filed: Apr. 8, 2019

(65) Prior Publication Data

US 2019/0369415 A1    Dec. 5, 2019

Related U.S. Application Data

(63) Continuation of application No. 14/800,469, filed on Jul. 15, 2015, now Pat. No. 10,254,564, which is a
(Continued)

(51) Int. Cl.
*G02C 7/04*     (2006.01)
*A61K 38/47*    (2006.01)
(Continued)

(52) U.S. Cl.
CPC ............ *G02C 7/047* (2013.01); *A61B 3/1005* (2013.01); *A61B 3/107* (2013.01); *A61K 9/0051* (2013.01);
(Continued)

(58) Field of Classification Search
CPC ......... A61B 3/107; A61B 8/10; A61B 3/1005; G02C 7/04; G02C 7/047; A61K 9/0051
(Continued)

(56) References Cited

U.S. PATENT DOCUMENTS

| 3,945,889 A | 3/1976 | Mima et al. |
| 3,957,049 A | 5/1976 | Neefe |

(Continued)

FOREIGN PATENT DOCUMENTS

| EP | 0 193 330 A2 | 9/1986 |
| EP | 0 459 148 A2 | 12/1991 |

(Continued)

OTHER PUBLICATIONS

Bennett et al., Troubleshooting Multifocal RGPs. Contact Lens Spectrum. Oct. 1, 1998. 1-2.
(Continued)

*Primary Examiner* — Kristina M Deherrera
(74) *Attorney, Agent, or Firm* — Wolf, Greenfield & Sacks, P.C.

(57) ABSTRACT

The disclosure relates to the use of contact lenses for treating ophthalmologic conditions, such as presbyopia, induced myopia, computer vision syndrome, insufficient accommodation, or a condition associated with insufficient accommodation. The contact lens may be selected based on a measured sagittal depth and/or eccentricity of the cornea. When fitted, fluid may accumulate between the cornea of the eye and the contact lens The lens may exhibit a sufficient amount of apical clearance such that when the wearer blinks, the lens moves no more than 1 mm on the eye. The lens and the eye may be structured such that bubbles greater than 0.5 mm in diameter are prevented from forming between the contact lens and the eye. The contact lens may be used in combination with a suitable bioactive agent providing for enhanced visual correction.

13 Claims, 8 Drawing Sheets

Related U.S. Application Data continuation of application No. 13/963,992, filed on Aug. 9, 2013, now Pat. No. 9,086,580.

(60) Provisional application No. 61/793,535, filed on Mar. 15, 2013, provisional application No. 61/682,008, filed on Aug. 10, 2012.

(51) Int. Cl.
| | |
|---|---|
| *A61B 3/10* | (2006.01) |
| *A61B 3/107* | (2006.01) |
| *A61K 9/00* | (2006.01) |
| *A61K 38/48* | (2006.01) |
| *A61F 9/013* | (2006.01) |

(52) U.S. Cl.
CPC .......... *A61K 38/47* (2013.01); *A61K 38/4886* (2013.01); *G02C 7/04* (2013.01); *G02C 7/049* (2013.01); *A61F 9/013* (2013.01); *C12Y 302/01035* (2013.01); *C12Y 304/24007* (2013.01)

(58) Field of Classification Search
USPC .......................................... 424/429; 351/247
See application file for complete search history.

(56) References Cited

U.S. PATENT DOCUMENTS

| | | | |
|---|---|---|---|
| 4,174,389 A * | 11/1979 | Cope ................. | A61K 38/4886 424/94.67 |
| 4,258,134 A | 3/1981 | Yoshida et al. | |
| 4,418,991 A | 12/1983 | Breger | |
| 4,484,922 A | 11/1984 | Rosenwald | |
| 4,525,043 A | 6/1985 | Bronstein | |
| 4,540,417 A | 9/1985 | Poler | |
| 4,571,039 A | 2/1986 | Poler | |
| 4,592,752 A | 6/1986 | Neefe | |
| 4,713,446 A | 12/1987 | DeVore et al. | |
| 4,759,746 A | 7/1988 | Straus | |
| 4,820,016 A | 4/1989 | Cohen et al. | |
| 4,851,513 A | 7/1989 | DeVore et al. | |
| 4,881,543 A | 11/1989 | Trembly et al. | |
| 4,897,349 A | 1/1990 | Swann et al. | |
| 4,904,594 A | 2/1990 | Karistam et al. | |
| 4,952,045 A | 8/1990 | Stoyan | |
| 4,969,912 A | 11/1990 | Kelman et al. | |
| 5,061,627 A | 10/1991 | Olsen et al. | |
| 5,144,630 A | 9/1992 | Lin | |
| 5,163,956 A | 11/1992 | Liu et al. | |
| 5,196,027 A | 3/1993 | Thompson et al. | |
| 5,201,764 A | 4/1993 | Kelman et al. | |
| 5,270,051 A | 12/1993 | Harris | |
| 5,316,926 A | 5/1994 | Brown et al. | |
| 5,354,331 A | 10/1994 | Schachar | |
| 5,465,737 A | 11/1995 | Schachar | |
| 5,484,432 A | 1/1996 | Sand | |
| 5,489,299 A | 2/1996 | Schachar | |
| 5,492,135 A | 2/1996 | DeVore et al. | |
| 5,496,726 A | 3/1996 | Park et al. | |
| 5,518,732 A | 5/1996 | Nigam | |
| 5,520,679 A | 5/1996 | Lin | |
| 5,529,076 A | 6/1996 | Schachar | |
| 5,580,570 A | 12/1996 | Robertson et al. | |
| 5,593,877 A | 1/1997 | King | |
| 5,626,865 A | 5/1997 | Harris et al. | |
| 5,695,509 A | 12/1997 | El Hage | |
| 5,722,952 A | 3/1998 | Schachar | |
| 5,747,027 A | 5/1998 | Stern et al. | |
| 5,756,552 A | 5/1998 | Takeuchi et al. | |
| 5,779,696 A | 7/1998 | Berry et al. | |
| 5,788,957 A | 8/1998 | Harris | |
| 5,792,103 A | 8/1998 | Schwartz et al. | |
| 5,815,237 A | 9/1998 | Vayntraub | |
| 5,827,721 A | 10/1998 | Stern et al. | |
| 5,866,120 A | 2/1999 | Karageozian et al. | |
| 5,894,002 A | 4/1999 | Boneberger et al. | |
| 5,963,297 A | 10/1999 | Reim | |
| 6,010,219 A | 1/2000 | Stovan | |
| 6,037,144 A | 3/2000 | Federov et al. | |
| 6,039,943 A | 3/2000 | Karageozian et al. | |
| 6,099,121 A | 8/2000 | Chapman et al. | |
| 6,123,938 A | 9/2000 | Stern et al. | |
| 6,132,735 A | 10/2000 | Harris et al. | |
| 6,161,544 A | 12/2000 | DeVore et al. | |
| 6,258,082 B1 | 7/2001 | Lin | |
| 6,261,545 B1 | 7/2001 | Okamoto | |
| 6,263,879 B1 | 7/2001 | Lin | |
| RE37,336 E | 8/2001 | Weigel et al. | |
| 6,296,847 B1 | 10/2001 | Gokcen et al. | |
| 6,335,006 B1 | 1/2002 | Miller | |
| 6,426,208 B1 | 7/2002 | Kakkis et al. | |
| 6,537,545 B1 | 3/2003 | Karageozian et al. | |
| 6,543,897 B1 | 4/2003 | Tung | |
| 6,551,590 B2 | 4/2003 | Karageozian et al. | |
| 6,569,661 B1 | 5/2003 | Qin et al. | |
| 6,585,971 B1 | 7/2003 | Kakkis | |
| 6,595,986 B2 | 7/2003 | Almeida | |
| 6,610,292 B2 | 8/2003 | Karageozian et al. | |
| 6,652,095 B2 | 11/2003 | Tung | |
| 6,710,051 B1 | 3/2004 | Trier | |
| 6,733,124 B2 | 5/2004 | Miyamura | |
| 6,737,075 B2 | 5/2004 | Karageozian | |
| 6,773,699 B1 | 8/2004 | Soltz et al. | |
| 6,780,840 B1 | 8/2004 | DeVore et al. | |
| 6,858,206 B2 | 2/2005 | Kakkis | |
| 6,875,427 B1 | 4/2005 | DeVore et al. | |
| 6,902,548 B1 | 6/2005 | Schuler et al. | |
| 6,939,364 B1 | 9/2005 | Soltz et al. | |
| 6,939,542 B2 | 9/2005 | Karageozian et al. | |
| 6,946,440 B1 | 9/2005 | DeWoolfson et al. | |
| 7,070,275 B2 | 7/2006 | Tung | |
| 7,346,416 B2 | 3/2008 | Wadding et al. | |
| 7,559,649 B2 | 7/2009 | Cotie et al. | |
| 8,366,272 B1 | 2/2013 | Myhill et al. | |
| 8,475,831 B2 | 7/2013 | Sancho | |
| 8,679,521 B2 | 3/2014 | Sancho | |
| 8,877,228 B2 | 11/2014 | Sancho | |
| 9,086,580 B2 * | 7/2015 | Grant .................... | A61B 3/107 |
| 9,241,980 B2 | 1/2016 | Osio | |
| 9,566,317 B2 | 2/2017 | Osio | |
| 9,931,382 B2 | 4/2018 | Osio Sancho | |
| 10,254,564 B2 | 4/2019 | Grant et al. | |
| 2002/0164316 A1 | 11/2002 | Karageozian et al. | |
| 2002/0185139 A1 | 12/2002 | Soll | |
| 2003/0139737 A1 | 7/2003 | Lin | |
| 2003/0170224 A1 | 9/2003 | Karageozian et al. | |
| 2003/0175259 A1 | 9/2003 | Karageozian et al. | |
| 2005/0080484 A1 | 4/2005 | Marmo et al. | |
| 2005/0146679 A1 | 7/2005 | Marmo et al. | |
| 2005/0256065 A1 | 11/2005 | Harris et al. | |
| 2007/0122450 A1 | 5/2007 | Sancho | |
| 2008/0024717 A1 | 1/2008 | Kim | |
| 2010/0082018 A1 | 4/2010 | Panthakey et al. | |
| 2012/0320334 A1 | 12/2012 | Ho et al. | |
| 2014/0043588 A1 | 2/2014 | Grant et al. | |
| 2014/0271597 A1 | 9/2014 | Osio | |
| 2015/0216952 A1 | 8/2015 | Osio | |
| 2016/0109725 A1 | 4/2016 | Grant et al. | |
| 2017/0266267 A1 | 9/2017 | Osio | |

FOREIGN PATENT DOCUMENTS

| | | |
|---|---|---|
| EP | 0235328 B1 | 4/1993 |
| EP | 0 608 341 A1 | 8/1994 |
| EP | 1 159 941 A2 | 12/2001 |
| JP | H04279525 A | 10/1992 |
| JP | 7-500267 A | 1/1995 |
| JP | 8-67617 A | 3/1996 |
| JP | 2003-513931 | 4/2003 |
| JP | 2003-517448 | 5/2003 |
| JP | 2005-534994 A | 11/2005 |
| JP | 2007-514760 A | 6/2007 |
| JP | 2007-195818 A | 8/2007 |

(56) References Cited

FOREIGN PATENT DOCUMENTS

| JP | 2007-534003 A | 11/2007 |
|----|---------------|---------|
| JP | 2008-112120 A | 5/2008 |
| JP | 4992051 B2 | 8/2012 |
| MX | PA05000125 A | 6/2006 |
| RU | 2166785 C1 | 5/2001 |
| RU | 2231814 C1 | 6/2004 |
| WO | WO 1991/016070 A1 | 10/1991 |
| WO | WO 1993/007840 A1 | 4/1993 |
| WO | WO 1994/002084 A1 | 2/1994 |
| WO | WO 1997/018835 A1 | 5/1997 |
| WO | WO 1998/052090 A1 | 11/1998 |
| WO | WO 1999/039238 A1 | 8/1999 |
| WO | WO 1999/040933 A1 | 8/1999 |
| WO | WO 1999/045869 A1 | 9/1999 |
| WO | WO 2000/030578 A1 | 6/2000 |
| WO | WO 2000/066139 A2 | 11/2000 |
| WO | WO 2001/034176 A1 | 5/2001 |
| WO | WO 2004/015479 A2 | 2/2004 |
| WO | WO 2005/062818 A2 | 7/2005 |
| WO | WO 2006/014681 A1 | 2/2006 |
| WO | WO 2010/099102 | 9/2010 |

OTHER PUBLICATIONS

Chu et al., Modern Orthokeratology. Peking University Medical Press. Aug. 31, 2006; 80-91.

Hesse, Using enzymes in the posterior eye segment. Current status and future possibilities. Ophthalmologe. Dec. 2001;98(12):1176-80. Review.

Humphrey, International standard for hyaluronidase. Bull World Health Organ. 1957;16(2):291-4.

Karpecki et al., The Science behind the "stain". Review of Optometry. Oct. 15, 2011.

Lui et al., Orthokeratology in low myopia. Part 1: efficacy and predictability. Cont Lens Anterior Eye. 2000;23(3):77-89.

Okada et al., Degradation of type IX collagen by matrix metalloproteinase 3 (stromelysin) from human rheumatoid synovial cells. FEBS Lett. Feb. 27, 1989;244(2):473-6.

Swarbrick et al., Orthokeratology review and update. Clin Exp Optom. May 2006;89(3):124-43.

Van Der Vorp, Beyond the Cornea. Global Contact. 2009;2,3.

Zhong et al., Practical Contact Lenses. Science Press. Jan. 1, 2004. 106-109.

* cited by examiner

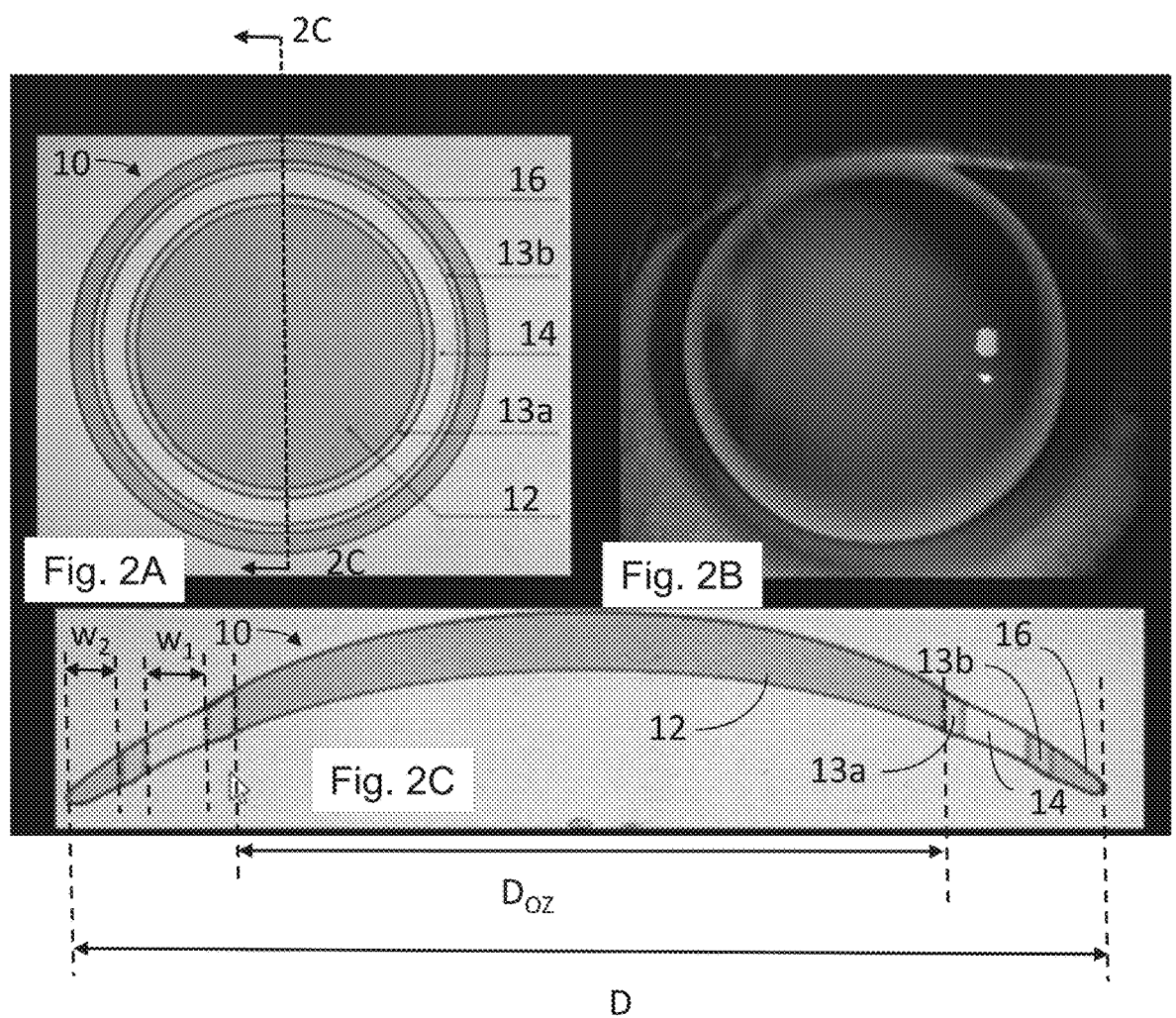

Keratometry
 SimK1: 40.90@ 89
 SimK2: 40.40@179
 CYL : -0.50
Asphericity 6.0mm
 e : 0.22 (-0.26, 0.71)
 Q: -0.22 (0.07, -0.50)
Pupilometry mm
 Photopic: 2.44
 Mesopic: 4.00
 MPdist: 0.08@ 90
 Pdist : 0.50@355
 Mdist : 0.50@ 5

| Patient | Far Vision before treatment | Near Vision before treatment | Far Vision 7 days Post | Near Vision 7 days Post | Far Vision 4 months Post | Near Vision 4 months Post | Far Vision 6 months Post | Near Vision 6 months Post | Far Vision 8 months Post | Near Vision 8 months Post |
|---|---|---|---|---|---|---|---|---|---|---|
| 1 | 20/20 | J8 | 20/20 | J3 | 20/15 | J2 | 20/15-1 | J1 | 20/15-1 | J1 |
| 2 | 20/20 | J6 | 20/15 | J3 | 20/15-1 | J3 | 20/15 | J2 | 20/15 | J2 |
| 3 | 20/20 | J10 | 20/15-3 | J10 | 20/15-1 | J6 | 20/15 | J5 | 20/15 | J5 |
| 4 | 20/20 | J10 | 20/20 | J3 | 20/15 | J4 | 20/15 | J5 | 20/15 | J5 |
| 5 | 20/25 | J8 | 20/15 | J3 | 20/15-1 | J3 | 20/20-1 | J2 | 20/20-1 | J2 |
| 6 | 20/15 | J10 | 20/15 | J3 | 20/20+2 | J5 | 20/20+2 | J5 | -- | -- |
| 7 | 20/20 | J10 | 20/15 | J1 | 20/15 | J2 | 20/15 | J2 | 20/15 | J1 |
| 8 | 20/25 | J6 | 20/20 | J2 | 20/20+3 | J3 | 20/15-1 | J2 | 20/15-1 | J2 |
| 9 | 20/20 | J10 | 20/15 | J6 | 20/15-1 | J4 | 20/15-2 | J5 | 20/15-2 | J5 |
| 10 | 20/25 | J10 | 20/20 | J10 | 20/20 | J10 | -- | -- | -- | -- |
| 11 | 20/20 | J5 | 20/15 | J2 | 20/15-1 | J3 | 20/15-1 | J3 | -- | -- |
| 12 | 20/25 | J8 | 20/15-1 | J3 | 20/15-2 | J3 | 20/15-2 | J3 | -- | -- |

Fig. 5A

CONTACT LENS USE IN THE TREATMENT OF AN OPHTHALMOLOGIC CONDITION

RELATED APPLICATIONS

The present application is a continuation of and claims priority under 35 U.S.C. § 120 to U.S. application Ser. No. 14/800,469, filed Jul. 15, 2015, which is a continuation of and claims priority under 35 U.S.C. § 120 to U.S. application Ser. No. 13/963,992, filed Aug. 9, 2013, which claims priority under 35 U.S.C. § 119(e) to U.S. provisional patent applications, U.S. Ser. No. 61/682,008, filed Aug. 10, 2012, and U.S. Ser. No. 61/793,535, filed Mar. 15, 2013, each of which is incorporated herein by reference.

FIELD OF THE INVENTION

Treatment of one or more ophthalmologic conditions are generally described. In particular, described are methods and systems for fitting and using the contact lenses discussed herein may provide a user with enhanced visual acuity.

BACKGROUND OF THE INVENTION

Contact lenses are lenses widely used to correct vision and are designed to be placed directly on the surface of the eye so as to cover a substantial portion of the cornea. A contact lens having particular curvature(s) bends light in a substantially even manner and is commonly used to correct various conditions of the eye.

Some contact lenses are made as orthokeratologic lenses which are designed to reshape the cornea so as to reduce refractive errors that may arise in certain ophthalmologic conditions. FIG. 1A depicts a conventional orthokeratologic contact lens having a largely hemispherical shape, where the lens is subdivided into various regions which may or may not have differing curvature(s). A toric contact lens exhibits focusing powers that will vary depending on the direction of incident light and is often used to correct for astigmatism. Multifocal contact lenses (e.g., bifocal lenses) are designed to have multiple focal points and are typically used to correct for presbyopia, which arises from the eye exhibiting a diminished ability (e.g., due to age) to focus on objects situated relatively close to the eye (e.g., reading material).

Some contact lenses are made from a soft material, such as a hydrogel or a silicone hydrogel. Silicone hydrogels are high in oxygen permeability relative to regular hydrogels. Rigid gas permeable lenses may be made from waterless polymers (e.g., non-hydrogel polymers) that are more rigid and generally smaller in diameter than hydrogel lenses. Rigid gas permeable lenses typically provide sharper vision than lenses made from a hydrogel and are commonly used as lenses for orthokeratologic treatment.

SUMMARY OF THE INVENTION

The inventors have recognized that one or more ophthalmologic conditions may be treated by the manner in which a contact lens is fitted to an eye. Such ophthalmologic conditions may include, but are not limited to, presbyopia, induced myopia, computer vision syndrome (CVS), insufficient accommodation, and other conditions arising from insufficient accommodation.

Methods in accordance with the present disclosure involve determining a radius of curvature at the flattest corneal meridian of the eye and a sagittal depth of the cornea of the eye, based on techniques that measure corneal topography. The method may also involve selecting a contact lens having an optic zone with a curvature that varies from a curvature at the flattest corneal meridian of the eye by between approximately 2.0 and approximately 6.0 diopters. The optic zone of the contact lens may have a radius of curvature equal to the sagittal depth of the cornea plus a distance of between approximately 0.05 mm and approximately 0.25 mm. The contact lens may be selected such that when the lens is suitably fitted onto the eye, a fluid volume (e.g., tear volume) between the cornea of the eye and the contact lens of between approximately 0.05 cubic mm and approximately 0.3 cubic mm is maintained.

In some embodiments, a contact lens fit for an eye may be structured so as to exhibit a sufficient amount of apical clearance such that the lens moves no more than 1 mm on the eye upon blinking. The contact lens may also be fit so that bubbles greater than 0.5 mm in diameter are prevented from forming between the contact lens and the surface of the eye.

The contact lens may have various regions configured and arranged with particular geometries (e.g., each region having a certain combination of curvature and diameter) that provide for enhanced vision correction, for example, by appropriate light refraction on the retina and/or, in some cases, reshaping the cornea and/or compensating for insufficient accommodation of the subject. The contact lens may be used in combination with one or more therapeutic agents (e.g., one or more corneal softening agents) to improve vision.

In an illustrative embodiment, a method of fitting a contact lens for an eye is provided. The method includes determining a radius of curvature at the flattest corneal meridian of the eye; and selecting a contact lens having an optic zone with a curvature that varies from a curvature at the flattest corneal meridian of the eye by between approximately 2.0 and approximately 6.0 diopters; and determining a sagittal depth of the cornea of the eye and selecting a contact lens having an optic zone with a radius of curvature equal to the sagittal depth of the cornea plus a distance of between approximately 0.05 mm and approximately 0.25 mm.

In another illustrative embodiment, a method of fitting a contact lens for an eye is provided. The method includes determining a radius of curvature at the flattest corneal meridian of the eye; and selecting a contact lens having an optic zone with a curvature that varies from a curvature at the flattest corneal meridian of the eye by between approximately 2.0 and approximately 6.0 diopters and such that, when the contact lens is fit on to the eye, a fluid volume between the cornea of the eye and the contact lens is maintained between approximately 0.05 cubic mm and approximately 0.3 cubic mm.

In a further illustrative embodiment, a method of using a contact lens for correcting vision is provided. The method includes placing a contact lens on a cornea of an eye of a subject such that, when the contact lens is fitted on the eye, a fluid volume between the cornea of the eye and the contact lens is maintained between approximately 0.05 cubic mm and approximately 0.3 cubic mm. The contact lens may include an optic zone having an optic zone diameter of between 7.0 mm and 9.0 mm and a radius of curvature of between approximately 7.0 mm and approximately 10.0 mm, and an inner peripheral region surrounding the optic zone, wherein inner peripheral region has a radius of curvature of between approximately 0.5 mm and approximately 1.5 mm greater than a radius of curvature of the optic zone.

In a further embodiment, provided is a method for treating an ophthalmologic condition, the method comprising using the contact lens as described herein, and applying one or more corneal softening agents to the eye of a subject suffering from or likely to suffer from the ophthalmologic condition. In certain embodiments, the condition being treated or prevented is presbyopia, induced myopia, computer vision syndrome (CVS), insufficient accommodation, or a condition associated with insufficient accommodation. In certain embodiments, the one or more corneal softening agents is selected from the group consisting of hyaluronidase, chondroitinase ABC, chondroitinase AC, endo B-galactosidase (keratanase), stromelysin (MM3), bacterial collagenase, interstitial collagenase (MM1), and gelatinase (MM2), and combinations thereof. In certain embodiments, the method comprises applying hyaluronidase and bacterial collagenase to the eye. In certain embodiments, the method comprises applying about 1 to about 10 USP units per mL hyaluronidase and about 5 to about 15 USP units per mL bacterial collagenase to the eye.

Advantages, novel features, and objects of the invention will become apparent from the following Detailed Description of the invention when considered in conjunction with the accompanying drawings, which are schematic and which are not intended to be drawn to scale. For purposes of clarity, not every component is labeled in every figure, nor is every component of each embodiment of the invention shown where illustration is not necessary to allow those of ordinary skill in the art to understand the invention.

BRIEF DESCRIPTION OF THE DRAWINGS

The accompanying drawings are not intended to be drawn to scale. In the drawings, each identical or nearly identical component that is illustrated in various figures is represented by a like numeral. Various embodiments of the invention are described, by way of example, with reference to the accompanying drawings, in which:

FIG. 2A is a top view of a contact lens in accordance with some embodiments;

FIG. 2B is a top view of the contact lens of FIG. 2A placed on an eye;

FIG. 2C is a section view through lines 2C-2C of the contact lens of FIG. 2A;

FIGS. 5A and 5B depict a Table (FIG. 5A) and corresponding bar graph (FIG. 5B) demonstrating improvement in near and far vision pre- and post-7 days, 1 month, 4 months, 6 months, and 8 months in presbyopic patients after treatment using an enzymatic formulation comprising hyaluronidase and bacterial collagenase in combination with a contact lens of the present invention. Near vision was measured using the Jaeger test scale. J1, J2=Font size 4 (fine print); J2, J3=Font size 5 (stocks); J4/J5=Font size 6 (yellow pages); J6=Font size 8 (newspaper); J8=Font size 10 (Adult books); J9-J11=Font size 14 (children's books); J11, J12=Font size 18 (large print).

DETAILED DESCRIPTION OF CERTAIN EMBODIMENTS OF THE INVENTION

Figure 1A:
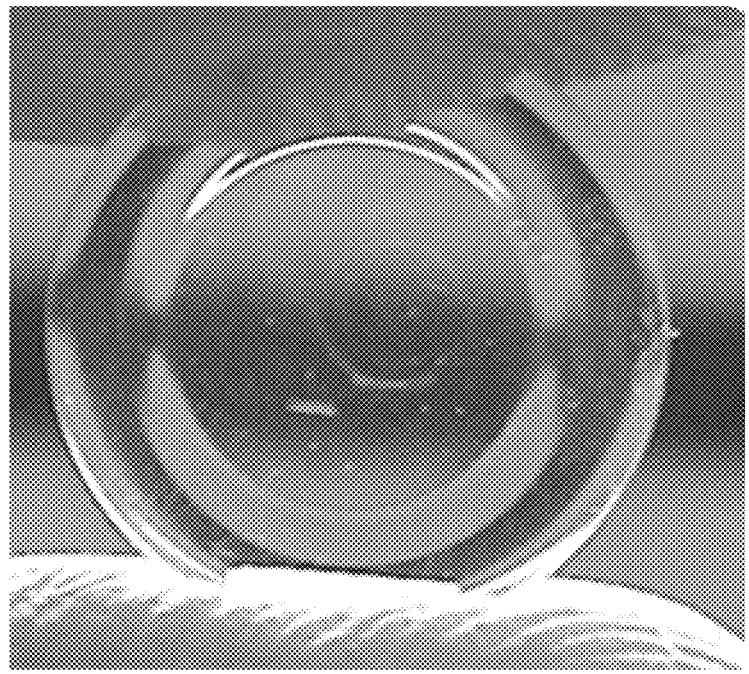
FIG. 1A is a perspective view of a conventional contact lens.

The present disclosure relates to the use of a contact lens for treating one or more ophthalmologic conditions. Methods described herein may result in improved vision correction based on certain characteristics such as geometric features of various regions of the contact lens in relation to the topography of the eye. These geometric features may depend, in part, on fit and prescription of the contact lens as determined via an optometric exam that incorporates a diagnostic fitting. Procedures and parameters for determining the appropriate fit and geometric shape of the contact lens are described herein and illustrated in the figures.

In some embodiments, contact lenses described herein may be useful for treating presbyopia. In some embodiments, contact lenses discussed herein may be useful to treat other conditions separate from or in addition to presbyopia, such as induced myopia, computer vision syndrome (CVS), insufficient accommodation, and conditions associated with insufficient accommodation. In some cases, certain types of contact lenses described herein are preferred for treating certain conditions. Alternatively, contact lenses described herein may be used to treat several different types of conditions.

Contact lenses in accordance with the present disclosure may include a number of regions that each exhibit a different curvature on the interior surface of the lens. Aspects of the present disclosure relate to a unique manner in which the respective curvature of different regions of the lens are selected according to their relationship to corneal topography. The geometric combination(s) of certain regions of the lens may result in a multi-focusing surface that corrects for any of the conditions discussed herein.

In selecting an appropriate contact lens, the optic zone of the lens may be selected to have a curvature that varies from the curvature at the flattest corneal meridian of the eye by between approximately 2.0 diopters and approximately 6.0 diopters. For instance, the curvature of the optic zone of the contact lens may be chosen to be greater, or less, than the curvature of the eye at the flattest corneal meridian by between approximately 2.0 and approximately 6.0 diopters (e.g., 2.5 D, 3.0 D, 3.5 D, 4.0 D, 4.5 D, 5.0 D, 5.5 D). The optic zone of the contact lens may have a radius of curvature equal to the sagittal depth of the cornea plus a distance of between approximately 0.05 mm and approximately 0.25 mm.

When the lens is properly fitted onto the eye, a fluid volume (e.g., tear volume) between the cornea of the eye and the contact lens of between approximately 0.05 cubic mm and approximately 0.3 cubic mm is maintained. In addition, when the lens is appropriately placed on the eye, there may be a sufficient amount of apical clearance such that when the wearer blinks, the lens moves no more than 1 mm on the eye. In some embodiments, when properly fitted to the eye of a subject, the contact lens is structured so that bubbles greater than 0.5 mm in diameter are prevented from forming between the contact lens and the eye.

Figure 1B:
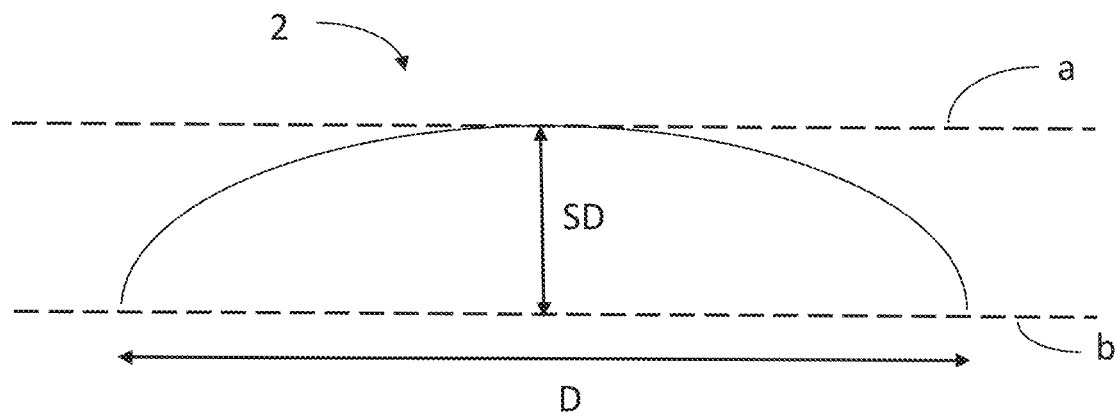
FIG. 1B is a section view through the apex of a contact lens.

FIG. 1B illustrates a section view of a contact lens 2 having a sagittal depth SD and an overall diameter D. The overall diameter is measured along the base plane b, which is shown in FIG. 1B and defined as a reference plane that lies flush with the outer edge surface of the contact lens. The sagittal depth SD is the distance measured from the apex of the contact lens perpendicular to the base plane b. The apex of the contact lens is the point at which the lens is flattest, defining an apical plane a that runs parallel to the base plane b. For a radially symmetric contact lens, the apex is also the highest point of the contact lens. In FIG. 1B, the contact lens has an arcuate surface that conforms to a generally smooth hemispherical-type shape (e.g., squashed hemisphere). However, it should be appreciated that contact lenses in accordance with the present disclosure are not required to conform to an exact hemispherical shape. For example, as described herein, contact lenses may include various regions that exhibit respective curvatures that are different from one another.

As discussed herein, the contact lens may include a region substantially central to the contact lens called the "optic zone." Generally speaking, when the contact lens is appropriately placed on the eye, the optic zone is the portion of the contact lens that provides for most, if not all, visual correction. In some cases, the optic zone may be surrounded around its periphery by another portion of the contact lens that does not affect vision. In other cases, portions surrounding the optic zone may contribute to visual correction and/or fit. Because contact lenses rest directly on the cornea of the eye, in some instances, the optic zone has approximately the same diameter as the pupil of the eye. For example, the optic zone itself and/or the edge of the optic zone may rest on the cornea. Though, in some embodiments, regions of the contact lens other than the optic zone, and/or the edge of the optic zone, may rest on the cornea of the eye. Or, in some embodiments, a contact lens (e.g., rigid gas permeable lens) may be fitted to the eye such that portions of the optic zone of the lens is spaced from the cornea of the eye so as to allow fluid (e.g., liquid, bubble formation, bioactive agent(s), etc.) to suitably collect, or otherwise pool, at appropriate regions between the lens and the eye. Accordingly, when the lens is suitably placed on the eye, certain regions of the lens may contact the surface of the eye (e.g., peripheral to the optic zone) and other regions of the lens (e.g., optic zone) may remain an appropriate distance from the surface of the eye.

In addition to the optic zone, the contact lens may have multiple regions each having different shapes (e.g., curvature) and sizes (e.g., width, diameter). In some embodiments, the optic zone of the contact lens refracts light entering into the eye which results in an improvement of visual acuity. The optic zone may be surrounded by an inner peripheral region, or an intermediate region. The inner peripheral region may be surrounded by an outer peripheral region. Various regions may be shaped to provide an appropriate reservoir for liquid (e.g., tears). For example, when the contact lens is placed on an eye, the optic zone and/or one of the peripheral regions may have a curvature that give rise to a suitable tear volume collection below the lens.

In some embodiments, the contact lens may be progressively flatter in curvature further from the center of the lens. For example, the inner peripheral region may be flatter than the optic zone and the outer peripheral region may be even flatter than the inner peripheral region. Such a structure may allow for the contact lens to appropriately fit comfortably and snugly on the eye. Though, it can be appreciated that contact lenses in accordance with the present disclosure might not exhibit progressively flatter characteristics in curvature further from the center of the lens. For example, in some embodiments, while the inner peripheral region may be flatter than the optic zone, the outer peripheral region may be steeper than the inner peripheral region. Or, the inner peripheral region may be steeper than the optic zone and the outer peripheral region may be steeper than the inner peripheral region.

A contact lens may include other regions, for example, an additional region that surrounds the outer peripheral region; a region located between the inner and outer peripheral regions; or a region located between the optic zone and the inner peripheral region. Alternatively, one or more of the above regions might not be present in various contact lens embodiments. For instance, in some embodiments, a contact lens may include only an optic zone and a single peripheral region.

One or more of each of the regions of the contact lens may function to reshape the cornea in accordance with orthokeratologic treatment. In some embodiments, when placed on the eye, various regions of the contact lens exert pressure on the corneal surface inducing physical alteration of the cornea. For example, portions of the contact lens (e.g., paracentral regions) may be appropriately steepened in a constant and uniform manner resulting in an improvement in fit and/or visual acuity. In some embodiments, the contact lens corrects the vision of a subject suffering from an ophthalmologic condition in combination with orthokeratological reshaping of the cornea, or alternatively, without orthokeratological reshaping of the cornea. In some embodiments, the contact lens described and shown in FIGS. 2A-2D may be useful to correct vision of a subject suffering from presbyopia, induced myopia, computer vision syndrome, insufficient accommodation, or a condition associated with insufficient accommodation.

Each of the optic zone, the inner peripheral region, and the outer peripheral region may have an appropriate radius of curvature which is determined as the distance from the center of a reference sphere that is coincident with the arc having a particular curvature that is defined by the inner (concave) surface of each region. As depicted in FIGS. 2A-2D, each of the optic zone, the inner peripheral region, and the outer peripheral region may have a respective width or diameter that falls within a suitable range.

FIGS. 2A-2C depict an illustrative embodiment of a contact lens 10 with various regions having different geometric configurations (e.g., having different curvatures, widths, diameters, etc.). The contact lens includes an optic zone 12, which, as noted above, is the primary portion of the contact lens that provides for visual correction, or at least a substantial part of correcting vision. In some cases, the optic zone of the contact lens may be structured such that, when the contact lens is placed on the eye, a suitable fluid volume (e.g., tears, bioactive composition/solution) collects between the lens and the eye. FIG. 2B depicts an example that shows such collection of fluid between the lens and the eye, as identified by a fluorescein marker.

As shown in FIG. 2A, the optic zone 12 is surrounded by an inner peripheral region 14. The inner peripheral region may or may not provide for visual correction. The inner peripheral region of the contact lens may have a radius of curvature that is greater, or less than, than the radius of curvature of the optic zone. That is, the curvature of the inner peripheral region of the lens may be more or less steep than the curvature of the optic zone of the lens.

Moving further radially outward, the inner peripheral region 14, in turn, is surrounded by outer peripheral region 16. The outer peripheral region 16 is shown in FIG. 2A to comprise the outer edge of the contact lens. The outer peripheral region of the contact lens may have a radius of curvature that is greater (or less than), in turn, than the radius of the curvature of each of the inner peripheral region and the optic zone.

The geometric configurations of the inner and outer peripheral regions may provide for an enhanced fit of the contact lens on to the cornea of the eye where, once suitably placed, the contact lens remains relatively centered over the cornea without substantial drift. In some embodiments, when placed on the eye, the entire contact lens is located on the cornea.

As further shown in FIG. 2C, the inner peripheral region 14 exhibits less curvature than that of the optic zone 12 and the outer peripheral region 16 exhibits less curvature than that of both the optic zone and the inner peripheral region. In other words, the contact lens is gradually flatter further from the center of the contact lens. In some cases, while not necessarily so, such a structure may provide for the collection of an appropriate tear volume between the contact lens and the eye while achieving a suitable fit. FIG. 2B depicts an embodiment of a contact lens placed on the cornea of an eye having a suitable fluid volume (e.g., tear volume) located between the contact lens and the eye.

In some embodiments, and as shown in FIGS. 2A and 2C, a first intermediate region 13a may be located between the optic zone 12 and the inner peripheral region 14, and a second intermediate region 13b may be located between the inner peripheral region 14 and the outer peripheral region 16. The intermediate regions 13a, 13b are shown in FIGS. 2A and 2C to be relatively narrow portions of the contact lens that are optionally disposed as transition(s) (e.g., blended transition regions) between portions of the contact lens having particular degrees of curvature. For instance, the first intermediate region 13a may exhibit a geometry (e.g., curvature) that comprises a blend of the respective geometries (e.g., curvatures) of the optic zone 12 and the inner peripheral region 14. Accordingly, the radius of curvature of the first intermediate region 13a may be between the respective radii of curvature of each of the optic zone 12 and the inner peripheral region 14. The geometry of the second intermediate region 13b may comprise a blend of the respective geometries of the inner peripheral region 14 and outer peripheral region 16. As such, the radius of curvature of the second intermediate region 13b may be between the respective radii of curvature of each of inner peripheral region 14 and outer peripheral region 16. Each of the first and second intermediate regions 13a, 13b may have a suitable width, typically less than the width of the inner or outer peripheral regions. However, in some cases, an intermediate region may have a width that is larger than the width of either of the inner or outer peripheral regions.

Figure 2D:
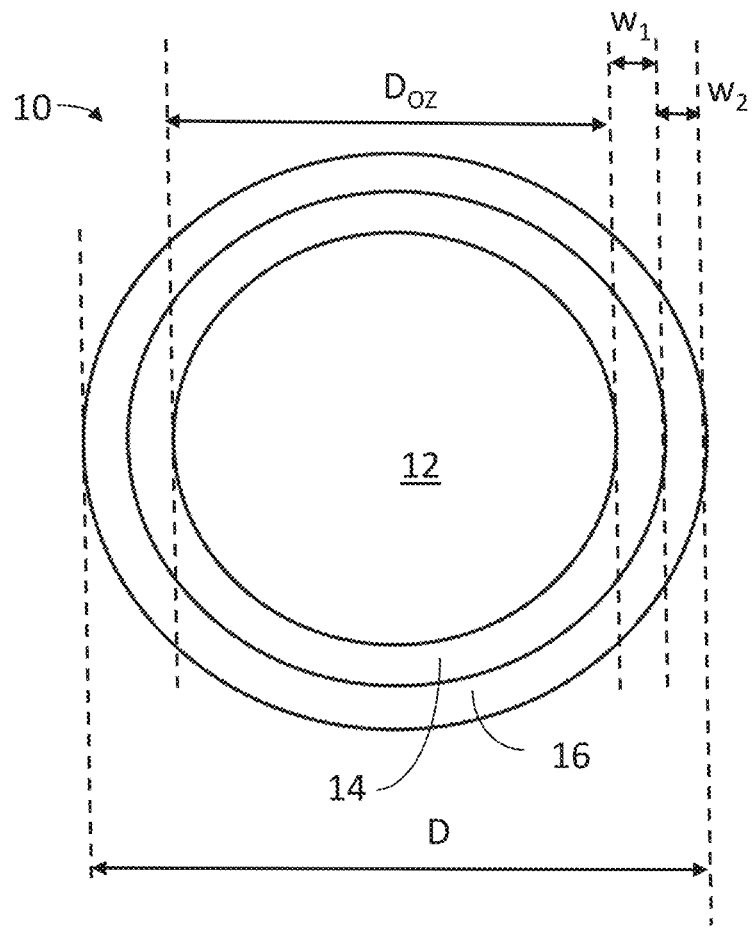
FIG. 2D is a top view of another contact lens in accordance with some embodiments.

As noted, inclusion of intermediate regions between the optic zone and inner/outer peripheral regions in the contact lens is optional. In some embodiments, there are no intermediate or transition regions located between the optic zone or inner and outer peripheral regions. FIG. 2D depicts an illustrative embodiment where the inner peripheral region 14 immediately surrounds the optic zone 12, and the outer peripheral region 16 immediately surrounds the inner peripheral region 14.

Depending on the prescription power and the type of vision to be corrected, the contact lens may have a suitable thickness. In some embodiments, if the contact lens has no prescription power, the thickness of the contact lens at approximately the center of the optic zone is approximately 0.18 mm. For every diopter of positive power in a contact lens that corrects for a particular ophthalmologic condition, the thickness may be increased or decreased by approximately 0.02 mm. For example, a lens suitable for correcting one ophthalmologic condition by +2 diopters may have a thickness of about 0.22 mm at approximately the center of the optic zone. In some cases, the lens may generally be flatter, or steeper, on the inside (concave) surface than on the outside (convex) surface. In another example, a lens suitable for correcting another ophthalmologic condition by −2 diopters may have a thickness of about 0.16 mm at approximately the center of the optic zone.

In some embodiments, the overall diameter D of the contact lens as measured along a reference base plane b that intersects the outer edge surface of the contact lens is between approximately 9.0 mm and approximately 11.0 mm (e.g., 9.2 mm, 9.4 mm, 9.6 mm, 9.8 mm, 10.0 mm, 10.5 mm). Though, in some cases, the overall diameter D of the contact lens may fall within a suitable range that is even broader, for example, between approximately 8.0 mm and approximately 12.0 mm, between approximately 8.5 mm and approximately 11.5 mm, between approximately 9.0 mm and approximately 11.0 mm, between approximately 9.5 mm and approximately 10.5 mm, or between approximately 9.5 mm and approximately 10.0 mm. In some embodiments, the overall diameter D of the contact lens is related to the optic zone diameter $D_{OZ}$. For example, if the optic zone diameter $D_{OZ}$ increases and the respective widths of the other regions remains constant, the overall diameter D of the contact lens will proportionately increase.

In some embodiments, the optic zone diameter $D_{OZ}$ of the contact lens, as shown in FIGS. 2A-2D and as measured along a chord that runs parallel to the reference base plane b, may be between approximately 7.5 mm and approximately 8.5 mm (e.g., 7.6 mm, 7.8 mm, 8.0 mm, 8.2 mm, 8.4 mm). The optic zone diameter $D_{OZ}$ of the contact lens may vary appropriately and, in some cases, fall within a suitable range, such as between approximately 6.0 mm and approximately 10.0 mm, between approximately 6.5 mm and approximately 9.5 mm, or between approximately 7.0 mm and approximately 9.0 mm.

The optic zone 12 of the contact lens may have a base curve having a curvature defined by a suitable radius of curvature (or base curve radius) as measured along the concave surface of the optic zone, facing toward the eye. In some embodiments, the degree of curvature of the optic zone is greater (steeper) than the degree of curvature of the cornea at its apex (e.g., at the flattest corneal meridian). In other words, for some embodiments, the radius of curvature of the optic zone of the contact lens is smaller than the radius of curvature of the eye at the apex of the cornea or where the cornea is flattest. Such a configuration may be helpful to achieve a suitable fit of the contact lens on the eye while achieving a suitable fluid volume between the contact lens and the eye.

The apex of the cornea may be determined using a number of techniques, such as by using corneal topography or keratometry. Corneal topography, generally, involves non-invasive medical imaging techniques for mapping the surface topography and/or curvature of the cornea. On a perfectly radially symmetric cornea, the apex is located at the geometric center of the cornea and at its highest point; however, the location of the apex may vary from person to person.

In accordance with methods described herein, the optic zone of a selected contact lens may have a curvature that is greater or less in degree than the curvature of the eye at the apex of the cornea (or region of the cornea having the flattest keratometry). In some embodiments, the degree of curvature of the optic zone may differ from the degree of curvature of the cornea at its apex (or at its flattest keratometry) by approximately 2.0 to 6.0 diopters. Depending on what type of vision correction is desired, the curvature of the optic zone of the contact lens may be selected accordingly. For example, the curvature of the optic zone of the contact lens may be greater than the curvature of the eye at the flattest corneal meridian by between approximately 2.0 and approximately 6.0 diopters (e.g., 2.5 D, 3.0 D, 3.5 D, 4.0 D, 4.5 D, 5.0 D, 5.5 D). Alternatively, in some cases, the curvature of the optic zone of the contact lens may be less than the curvature of the eye at the flattest corneal meridian by between approximately 2.0 diopters and approximately 6.0 diopters (e.g., 2.5 D, 3.0 D, 3.5 D, 4.0 D, 4.5 D, 5.0 D, 5.5 D).

It can be appreciated that the range of adjustment of curvature of the optic zone of the contact lens as compared to the curvature of the eye at the apex of the cornea may vary appropriately. For instance, an adjustment range of curvature between the optic zone of the contact lens and the eye at the apex of the cornea may be between approximately 2.0 and approximately 7.0 diopters, between approximately 2.5 and approximately 6.5 diopters, between approximately 3.0 and approximately 6.0 diopters, or between approximately 3.5 and approximately 5.5 diopters.

Table 1 provides a listing of the corresponding values for radius of curvature of an optic zone and overall contact lens diameter of a contact lens based on diopter measurements provided from a keratometer. Accordingly, an increase in keratometric diopters in the optic zone corresponds to a decrease in the radius of curvature of the optic zone (leading to a greater degree of curvature) and a decrease in the overall diameter D of the contact lens. Conversely, a decrease in keratometric diopters in the optic zone corresponds to an increase in the radius of curvature of the optic zone (leading to a lesser degree of curvature) and an increase in the overall diameter D of the contact lens.

TABLE 1

Radius of curvature of the optic zone and diameter of the contact lens based on keratometric diopters of the optic zone.

| Keratometric Diopters (D) of the Optic Zone | Radius of Curvature (mm) of the Optic Zone | Overall Contact Lens Diameter (mm) |
|---|---|---|
| 48.28-51.92 | 6.99-6.50 | 9.4 |
| 45.06-48.21 | 6.99-7.00 | 9.6 |
| 42.24-45.00 | 7.99-7.50 | 9.6 |
| 39.75-42.18 | 8.49-8.00 | 9.8 |
| 37.54-39.70 | 8.99-8.50 | 9.8 |
| 35.56-37.50 | 9.49-9.00 | 10 |
| 33.78-35.52 | 9.99-9.50 | 10 |

It can be appreciated that the optic zone of the contact lens may have a base curve radius of curvature that falls within a suitable range. In some embodiments, the radius of curvature of the optic zone is between approximately 5.0 mm and approximately 11.0 mm, between approximately 6.0 mm and approximately 10.0 mm, between approximately 7.0 mm and approximately 10.0 mm, or between approximately 7.0 mm and approximately 9.0 mm.

Aspects of the present disclosure provide for a non-surgical, non-invasive method for effectively treating presbyopia or other ophthalmologic condition over extended periods of time. In some embodiments, orthokeratologic methods are used to alter corneal physiology, including the dioptric power of the cornea, through an interactive technique of fitting the eye to a contact lens that alters the shape of the cornea (thereby altering refractive power). In some embodiments, prescribed contact lenses are worn in a manner that reshapes the cornea, and a pharmaceutical composition formulated for the patient is administered, in part, to allow for reshaping of the cornea. The contact lenses may be chosen based on a number of factors, such as the different base curves of the posterior and anterior curvatures, the optical diameter of the optic zone, and the multiple regions peripheral to the optic zone. In some cases, the contact lens exerts pressure on the corneal surface, thereby steepening portions of the paracentral cornea in a concentric manner.

In some embodiments, the radius of curvature of the optic zone of the contact lens is determined with respect to the sagittal depth of the cornea. In an example, for a contact lens having an optic zone diameter of 8.0 mm, the optic zone has a radius of curvature equal to the sagittal depth of the cornea plus 0.1511 mm+/−0.0285 mm. In some embodiments, the optic zone may have a radius of curvature equal to the sagittal depth of the cornea plus a distance of between approximately 0.01 mm and approximately 0.4 mm, between approximately 0.03 mm and approximately 0.35 mm, between approximately 0.04 mm and approximately 0.3 mm, between approximately 0.05 mm and approximately 0.25 mm, between approximately 0.07 mm and approximately 0.23 mm, between approximately 0.1 mm and approximately 0.2 mm, between approximately 0.1 mm and approximately 0.15 mm, between approximately 0.15 mm and approximately 0.2 mm, or between approximately 0.12 mm and approximately 0.18 mm. It can be appreciated that the radius of curvature of the optic zone of the lens may vary outside of the above noted ranges and may be applicable for contact lenses having a variety of optic zone diameters and for eyes with corneas that exhibit a wide range of sagittal depth values.

The sagittal depth of a cornea (Sag) over an optic zone diameter (e.g., having a $D_{OZ}$ of 8.0 mm) may be determined according to the following formula:

$$\text{Sag} = \frac{R_o - \sqrt{R_o^2 - y^2(1-e^2)}}{1-e^2}$$

where $R_o$=Apical Radius, y=½ Chord diameter, e=corneal eccentricity. Such values may be measured according to methods known in the art for determining the topography of the eye. The corneal eccentricity may be determined by fitting an ellipse to the topography of the cornea based on measurements taken, for example, by corneal topography or a keratometer. In general, the greater the corneal eccentricity, the lower the sagittal depth of the cornea. In some embodiments, the radius of curvature of the optic zone of the contact lens is determined with respect to the eccentricity of the cornea.

The sagittal depth SD of a contact lens may vary appropriately from the sagittal depth of the cornea so as to achieve a desirable fit and fluid/tear volume. For example, if the sagittal depth SD of the contact lens is excessive, after the contact lens is placed on the eye, fluid may pool disproportionately with the significant possibility for bubbles to undesirably arise. If the sagittal depth SD of the contact lens is insufficient, the contact lens might not fit well on the eye, leading to improper alignment of the lens and/or rocking of the contact lens on the cornea. Accordingly, the fit of a contact lens on the eye may depend, at least in part, on the sagittal depth and/or eccentricity of the cornea with respect to the curvature of the optic zone of the contact lens.

As discussed above, the geometric configuration of the contact lens with respect to the eye may result in a fluid volume (e.g., tear volume) maintained for a suitable period of time between the cornea and the optic zone of the contact lens. In an example, such a fluid volume may be about 0.183 cubic mm+/−0.047 cubic mm. In some embodiments, when the contact lens is placed on the eye, the fluid volume between the cornea and the optic zone of the contact lens is maintained at an amount of between approximately 0.01 cubic mm and approximately 0.5 cubic mm, between approximately 0.03 cubic mm and approximately 0.45 cubic mm, between approximately 0.04 cubic mm and approximately 0.4 cubic mm, between approximately 0.05 cubic mm and approximately 0.3 cubic mm, between approximately 0.1 cubic mm and approximately 0.25 cubic mm, between approximately 0.05 cubic mm and approximately 0.2 cubic mm, between approximately 0.2 cubic mm and approximately 0.3 cubic mm, or between approximately 0.12 cubic mm and approximately 0.23 cubic mm. The fluid/tear volume may be maintained between the cornea and the contact lens for an extended period of time, for example, any of the treatment periods described further below. It can be appreciated that, when the contact lens is suitably fit on to the eye, the fluid/tear volume that is maintained between the cornea of the eye and the contact lens may vary outside of the above noted ranges.

Contact lenses described herein may be fitted onto a subject's eye, based on the overall topography of the cornea. That is, in a diagnostic fit, other aspects of the cornea besides the curvature at the flattest keratometry are taken into account, such as the sagittal depth and the corneal eccentricity. In some embodiments, contact lens are fit so that fluid is able to pool centrally between the contact lens and the cornea which, in some cases, may be in contrast to how conventional gas permeable contact lens are fit. In addition to allowing an appropriate volume of fluid/tears to be trapped or otherwise maintained between the contact lens and the cornea, sufficient apical clearance of the lens may be achieved such that the lens does not move more than 1 mm (or more than 0.2 mm, more than 0.4 mm, more than 0.6 mm, more than 0.8 mm, more than 1.2 mm, more than 1.4 mm, more than 1.6 mm, more than 1.8 mm, more than 2 mm, more than 2.5 mm, etc.) on the eye upon blinking. It should be appreciated that when a particular volume of fluid is maintained between the contact lens and the cornea, fluid and gas exchange between the surrounding environment and the space between the lens and the eye may occur. Further, such fitting of the contact lens may be such that bubbles greater than 0.5 mm (or greater than 0.2 mm, greater than 0.4 mm, greater than 0.6 mm, greater than 0.8 mm, greater than 1 mm, etc.) in diameter are prevented from forming between the contact lens and the surface of the eye.

The inner peripheral region 14 of the contact lens may have a suitable width $W_1$, as measured along a reference direction that runs parallel to the base plane b consistently around the circumference of the contact lens. In some embodiments, the width $W_1$ of the inner peripheral region of the contact lens is between approximately 0.35 mm and approximately 0.45 mm (e.g., 0.36 mm, 0.38 mm, 0.4 mm, 0.42 mm, 0.44 mm). The width $W_1$ of the inner peripheral region may fall within an appropriate range broader than the above noted range, for example, between approximately 0.10 mm and approximately 0.70 mm, between approximately 0.20 mm and approximately 0.60 mm, between approximately 0.25 mm and approximately 0.55 mm, or between approximately 0.30 mm and approximately 0.50 mm. It should be understood that other values of the width $W_1$ are also possible.

The inner peripheral region 14 of the contact lens may also have a suitable radius of curvature as measured along the concave surface of the inner peripheral region, facing toward the eye. In some embodiments, the radius of curvature of the inner peripheral region 14 of the contact lens is greater than the radius of curvature of the optic zone 12 around which the inner peripheral region surrounds. That is, the degree of curvature of the inner peripheral region 14 may be less than the degree of curvature of the optic zone 12. In some cases, the curvature of the inner peripheral region may provide space for a tear reservoir so that fluid does not accumulate substantially at the region directly between the optic zone of the contact lens and the cornea. Though, it can be appreciated that other geometries are possible, for example, the degree of curvature of the inner peripheral region 14 may be greater than the degree of curvature of the optic zone 12.

In some embodiments, the inner peripheral region 14 of the contact lens may have a radius of curvature that is greater than the radius of curvature of the optic zone of the contact lens by an amount between approximately 0.7 mm and approximately 1.2 mm (e.g., 0.7 mm, 0.9 mm, 1.1 mm). The amount by which the radius of curvature of the inner peripheral region 14 is greater than the radius of curvature of the optic zone may vary outside of the above noted range. For example, the radius of curvature of the inner peripheral region of the contact lens may be greater than the radius of curvature of the optic zone by a range of between approximately 0.1 mm and approximately 2.0 mm, between approximately 0.3 mm and approximately 1.5 mm, or between approximately 0.5 mm and approximately 1.5 mm. In some embodiments, the radius of curvature of the inner peripheral region 14 is between approximately 5.5 mm and approximately 12.0 mm, between approximately 6.0 mm and approximately 11.5 mm, between approximately 7.0 mm and approximately 10.5 mm, between approximately 8.0 mm and approximately 10.0 mm (e.g., 8.5 mm, 9.0 mm, 9.5 mm), or any other suitable range.

As shown in FIGS. 2A and 2C, the outer peripheral region 16 of the contact lens surrounds both the optic zone 12 and the inner peripheral region 14. The outer peripheral region 16 may have a suitable width $W_2$, as measured along a reference direction that runs parallel to the base plane b consistently around the circumference of the contact lens. In some embodiments, the width $W_2$ of the outer peripheral region of the contact lens is between approximately 0.35 mm and approximately 0.45 mm (e.g., 0.36 mm, 0.38 mm, 0.4 mm, 0.42 mm, 0.44 mm). The width $W_2$ of the outer peripheral region may fall within an appropriate range, such as between approximately 0.20 mm and approximately 0.60 mm, between approximately 0.25 mm and approximately 0.55 mm, or between approximately 0.30 mm and approximately 0.50 mm. It can be appreciated that other values of the width $W_2$ are possible.

The outer peripheral region 16 of the contact lens may also have a suitable radius of curvature as measured along the concave surface of the outer peripheral region, facing toward the eye. In some embodiments, the outer peripheral region 16 of the contact lens may have a radius of curvature ranging between approximately 10.8 mm and approximately 11.8 mm (e.g., 10.8 mm, 11.0 mm, 11.3 mm, 11.5 mm, 11.8 mm). The radius of curvature of the outer peripheral region 16 may vary outside of the above noted range. For example, the radius of curvature of the outer peripheral region of the contact lens may be between approximately 9.0 mm and approximately 14.0 mm, between approximately 9.5 mm and approximately 13.0 mm, between approximately 10.0 mm and approximately 12.5 mm, between approximately 10.5 mm and approximately 12.0 mm, or any other suitable range.

Similar to that noted previously with respect to the inner peripheral region, the radius of the curvature of the outer peripheral region may vary according to the radius of curvature of the optic zone. In some embodiments, the radius of curvature the outer peripheral region 16 of the contact lens may have a radius of curvature that is greater than the radius of curvature of the optic zone of the contact lens by an amount between approximately 2.0 mm and approximately 5.0 mm (e.g., 2.5 mm, 3.0 mm, 3.5 mm, 4.0 mm, 4.5 mm). Or, the radius of curvature of the outer peripheral region may be greater than the radius of curvature of the optic zone by a range of between approximately 1.0 mm and approximately 6.0 mm, or between approximately 1.5 mm and approximately 5.5 mm. For example, when the radius of curvature of the optic zone is between approximately 7.0 mm and approximately 7.5 mm, the radius of curvature of the outer peripheral region may be approximately 11.0. As another example, when the radius of curvature of the optic zone is between approximately 7.5 mm and approximately 8.5 mm, the radius of curvature of the outer peripheral region may be approximately 11.5.

Diagnostic lens fitting may be used to determine the appropriate relationship between a contact lens and the cornea upon which the lens will sit, for a suitable contact lens to be selected. An ideal contact lens fit involves a contact lens that is perfectly centered, or almost perfectly, moves 1 mm or less (e.g., 0.5 to 1.0 mm) upon blinking, does not develop excessive bubble formation, and exhibits apical clearance. Apical clearance arises when a suitable distance exists between the posterior surface of the contact lens and the apex of the cornea. As noted above, while the contact lens may exhibit apical clearance, a proper fit between the contact lens and the eye also prevents the formation of air bubbles in excess of 0.5 mm in diameter, or in excess of 1.0 mm in diameter, between the optic zone of the contact lens and the eye. In some embodiments, contact lenses are chosen to be the steepest possible on the eye while not having an air bubble having a diameter of larger than 0.5 mm to 1.0 mm between the optic zone and the eye.

Figure 3A:
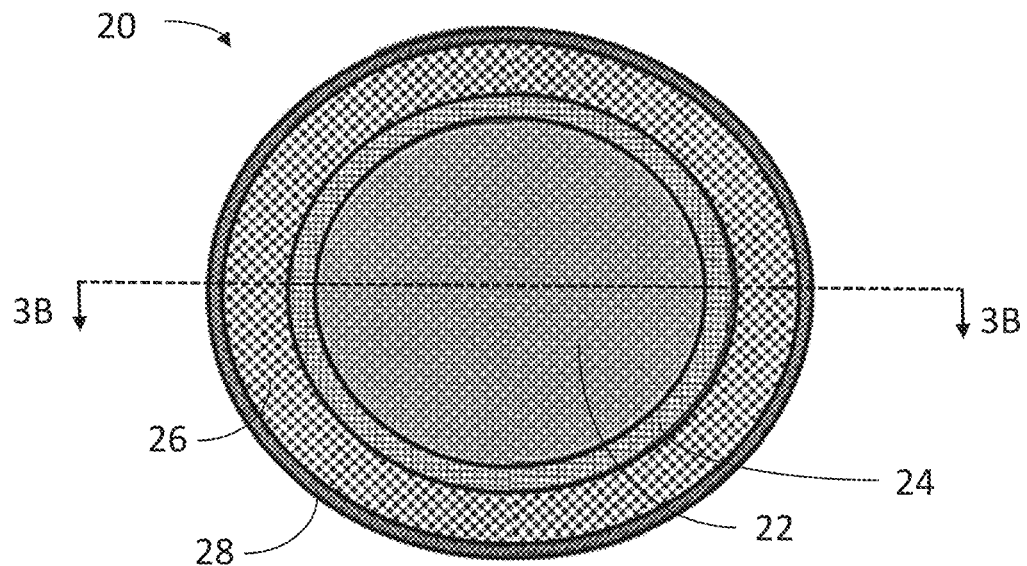
FIG. 3A is a top view of another contact lens in accordance with some embodiments.
Figure 3B:
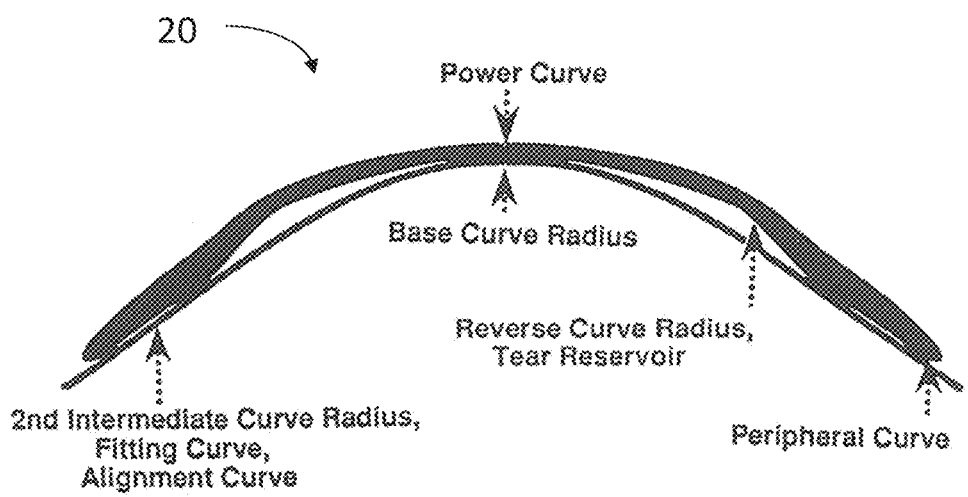
FIG. 3B is a section view through lines 3B-3B of the contact lens of FIG. 3A.

A contact lens 20 that may be well suited for orthokeratologic treatment is illustrated in FIGS. 3A-3B. As shown, the optic zone 22 is surrounded by an inner peripheral region 24. In some embodiments, the optic zone 22 and/or the inner peripheral region 24 is shaped to provide a reservoir for liquid (e.g., tears) to accumulate without detrimentally affecting vision. The inner peripheral region 24 may be surrounded by an intermediate region 26. The intermediate region 26 may be surrounded by an outer peripheral region 28. The intermediate 26 and outer peripheral region 28 may be shaped for the contact lens to appropriately fit snugly and comfortably on the eye. Each of the regions noted may have a certain geometry that contributes to overall vision improvement. Other regions may be included or certain regions may be excluded. When appropriately placed on the eye, the optic zone of the lens may rest directly on the cornea so as to refract a majority of the light entering into the eye to be focused on the retina, improving visual acuity.

The optic zone 22 includes a base curve having a curvature defined by a base curve radius (i.e., radius of curvature) at the inner (concave) surface of the lens and a power curve at the outer (convex) surface of the lens. The base curve radius will vary primarily depending on fit of the contact lens on the eye. The power curve will vary depending on the prescription of the lens which affects overall thickness of the contact lens. In various embodiments, the optic zone of the contact lens may have a thickness that depends on the power of the contact lens prescription. For instance, when correcting for certain opthalmologic conditions, the thickness of the optic zone may be greater or lesser.

The inner peripheral region 24 of the contact lens illustrated in FIGS. 3A-3B exhibits a greater degree of curvature than that of the optic zone—such a region is shown as having a reverse curve radius. That is, the radius of curvature of the inner peripheral region 24 is smaller than the radius of curvature of the optic zone. In some embodiments, such a structure may form a tear reservoir which allows a suitable tear volume to gather peripheral to the optic zone.

The intermediate region 26 and outer peripheral region 28 may exhibit suitable degrees of curvature, respectively, allowing for an appropriate fit of the contact lens on the eye. In some embodiments, and as shown in FIG. 3B, the radii of curvature of each of the intermediate and outer peripheral regions 26, 28 is greater than the radius of curvature of the inner peripheral region 24.

As further noted above, contact lenses and diagnostic fitting techniques described herein may be well suited in correcting for presbyopia and/or other opthalmologic conditions. Fitting and prescribing a contact lens depends, in part, on the shape of the eye and the type of vision to be corrected (i.e., presbyopia, induced myopia, computer vision syndrome, amongst others). An optometric exam generally involves measuring the topography of the eye and determining what degree of optical correction is required to achieve a suitable level of visual acuity, for both eyes and for each eye separately. A contact lens prescription often includes a record of the material recommended to be used for the contact lens, the base curve radius (i.e., radius of curvature of the concave inner surface of the optic zone), the overall diameter D of the contact lens, the power of the lens in diopters, and the thickness of the center of the contact lens.

In some embodiments, when correcting for certain conditions, such as presbyopia, a contact lens is selected so that it exhibits the steepest possible curvature on the eye while not giving rise to the formation of air bubbles (or air bubbles that are larger than a threshold size). The contact lens would also be chosen so that it centers suitably well on the eye and moves 0.5 to 1.0 mm or less on each blink. During a fitting procedure, a topographical map may be taken of the eye to assess the corneal curvature and eccentricity. To provide the subject with an initial fit, a diagnostic lens having an appropriate adjustment in curvature based on the topographical map of the eye may be used. Then, over-refraction may be assessed to determine the proper power of the lens. For instance, as discussed further in Example 1, if an eye at the flattest keratometry is determined to have a curvature of 40.6 D and an eccentricity (asphericity) of 0.22, a diagnostic lens of 45 D may be used to initially fit the patient. Various aspects of the fit, such as apical clearance, may be assessed based on appropriate diagnostic methods (e.g., using fluorescein imaging). Then, the level of over-refraction is determined. For example, if the power of the diagnostic lens is −5.5 D and the over-refraction is determined to be +1.25 D, then a contact lens having a power of −4.25 D may be chosen in the final prescription, with the appropriate fitting dimensions.

In some embodiments, when correcting for one or more ophthalmologic conditions, the optometric exam may involve determining a suitable prescription and radius of curvature of the concave surface of the optic zone of the contact lens. In some embodiments, the base curve radius of curvature of the optic zone of the contact lens is determined by first measuring the radius of curvature of the cornea, in diopters, at the flattest keratometry (at the apex of the cornea). Subsequently, referencing Table 1 to determine the relationship between optical power in diopters and radius of curvature of the optic zone, a suitable adjustment amount or curvature correction value of the radius of curvature of the optic zone is added (e.g., 3.5-5.5 diopters, 3.50 diopters). For example, if the flattest keratometry is determined to be 41.50 diopters, the addition of 3.50 diopters as a suitable adjustment amount leads to a total of 45.00 diopters. Based on Table 1, 45.00 diopters is equivalent to a radius of curvature of the concave surface of the optic zone of 7.50 mm.

The contact lens may include any suitable material that allows for comfortable placement of the contact lens on the eye so as to provide for vision correction. In some embodiments, the contact lens is made up of a gas permeable material having an appropriate degree of permeability. For example, the contact lens may be made out of a siloxanyl fluoromethacrylate copolymer that exhibits substantial gas permeability (e.g., BOSTON XO having a permeability greater than 100 measured as transmissibility per thickness). In some embodiments, the contact lens is composed of a gas permeable material having a transmissibility per thickness of between approximately 50 and approximately 500, between approximately 100 and approximately 400, or between approximately 150 and approximately 300.

Contact lenses may be manufactured by any suitable method. In some embodiments, contact lenses are spin-cast where liquid silicone or another suitable material is spun in a revolving mold at high speeds. Or, similarly, molten lens material may be added to a rotating mold and shaped by centrifugal forces. Alternatively, contact lenses may be diamond-turned by cutting of a cylindrical disk in a lathe and polishing of the concave and convex surfaces of the lens with a fine abrasive. Such a process may be used to form both rigid and soft lenses. In some cases, contact lenses may be manufactured by injection molding. For example, the contact lens material may be moistened throughout the casting and molding process and appropriately hydrated to form. Other methods of manufacture may be employed. Conventional methods for making contact lenses are disclosed in U.S. Pat. No. 5,815,237, entitled "Contact Lens and Method for Making the Same"; U.S. Pat. No. 5,894,002, entitled "Process and Apparatus for the Manufacture of a Contact Lens"; and U.S. Pat. No. 7,346,416, entitled "Contact Lens Manufacture," each of which is incorporated herein by reference in its entirety.

Treatment Methods

As understood from the present disclosure, the present disclosure further relates to the use and fitting of a contact lens in combination with one or more corneal softening agents to the eye for the treatment of an ophthalmologic condition from which a subject is suffering from or likely to suffer from. Such a treatment method comprises applying the contact lens and one or more corneal softening agents to the eye of the subject. In certain embodiments, the treatment method further comprises applying one or more therapeutic agents to the eye of the subject. In certain embodiments, the ophthalmologic condition may be present in one eye or both eyes.

As used herein, "applying" in the context of corneal softening agents and therapeutic agents ("agents"), refers to administering the one or more agents topically to the eye or injecting into the eye (e.g., the cornea of the eye). "Applying" in the context of the contact lens refers to placing the lens on the eye.

In certain embodiments, the treatment method comprises applying an effective amount of the one or more agents. As used herein, an "effective amount" refers to the amount of one or more agents necessary to elicit the desired biological response, e.g., in the instance of corneal softening agents, reshaping the cornea thereby improving the subject's vision (e.g., near vision and/or far vision). As will be appreciated by those of ordinary skill in this art, the effective amount of an agent may vary depending on such factors as the desired biological endpoint, the condition being treated, the mode of administration, and the age, health, and condition of the subject. An effective amount encompasses therapeutic and prophylactic (preventative) treatment.

As used herein, and unless otherwise specified, the terms "treat," "treating" and "treatment" contemplate an action that occurs while a subject is suffering from the specified condition which reduces the severity of the condition or retards or slows the progression of the condition ("therapeutic treatment"), and also contemplates an action that occurs before a subject begins to suffer from the condition and which inhibits or reduces the severity of the condition ("prophylactic treatment").

As used herein, and unless otherwise specified, a "therapeutically effective amount" refers to an amount of an agent or combination of agents sufficient to provide a therapeutic benefit in the treatment of the condition or to delay or minimize one or more symptoms associated with the condition. The term "therapeutically effective amount" can encompass an amount that improves overall therapy, reduces or avoids symptoms or causes of the condition, or enhances the therapeutic efficacy of another agent.

As used herein, and unless otherwise specified, a "prophylactically effective amount" refers to an amount of an agent or combination of agents sufficient to prevent a condition or one or more symptoms associated with the condition, or to prevent recurrence. The term "prophylactically effective amount" can encompass an amount that improves overall prophylaxis or enhances the prophylactic efficacy of another prophylactic agent.

A "subject" to which administration is contemplated includes human subjects (i.e., a male or female of any age group, e.g., a pediatric subject (e.g, a child between 2 to 10 years old, an adolescent between 11 to 19 years old) or adult subject (e.g., a young adult between 20 to 40 years old, a middle-aged adult between 41 to 64 years old, or a senior adult between 65 to 100 years old)). Other non-human animals, for example mammals (e.g., primates (e.g., cynomolgus monkeys, rhesus monkeys); and commercially relevant mammals such as rabbits, cattle, pigs, horses, sheep, goats, cats, and/or dogs, are also contemplated as subjects. The non-human animal may be a male or female and at any stage of development.

Upon cessation of the treatment, unlike traditional orthokeratology, the condition and pre-treatment symptoms are not expected to return within 24 to 48 hours, but instead are expected to return no earlier than 1 month (e.g., 2, 3, 4, 5, 6, 7, 8, 9, 10, 11, or 12 months) after the treatment period has ended. At the time that the condition and pre-treatment symptoms return, the subject may choose to repeat the treatment method. In certain embodiments, the treatment results in corrected vision for at least 1 month to at least one year, for at least 2 months to at least one year, for at least 3 months to at least one year, for at least 4 months to at least one year, for at least 5 months to at least one year, for at least 6 months to at least one year, for at least 7 months to at least one year, for at least 8 months to at least one year, for at least 9 months to at least one year, for at least 10 months to at least one year, or for at least 11 months to at least 1 year, e.g., the treatment results in corrected vision for at least 1, 2, 3, 4, 5, 6, 7, 8, 9, 10, 11, or 12 months. In certain embodiments, the treatment results in corrected vision for over 1 year, e.g., over 1 year, over 2 years, over 3 years, over 4 years, or over 5 years.

In certain embodiments, the treatment period (i.e., the time period during which the method is practiced) is between 3 days to 14 days, e.g., between 3 to 10 days, between 3 to 7 days, between 4 to 7 days, between 4 to 6 days, between 3 to 6 days, or between 3 to 5 days, inclusive, e.g., the treatment period is 3, 4, 5, 6, 7, 8, 9, 10, 11, 12, 13, or 14 days. In certain embodiments, however, the treatment period is longer than 14 days, e.g., at least 3 weeks, at least 4 weeks, at least 5 weeks, or even longer than 5 weeks.

In certain embodiments, the treatment method comprises applying the contact lens to the eye for about 1 hour to about 24 hours per day during the treatment period, e.g., for about 1 hour to about 18 hours, for about 1 hour to about 15 hours, for about 1 hour to about 10 hours, for about 1 hour to about 8 hours, for about 1 hour to about 6 hours, for about 1 hour to about 4 hours, for about 1 hour to about 2 hours, for about 2 hours to about 18 hours, for about 2 hours to about 15 hours, for about 2 hours to about 10 hours, for about 2 hour to about 8 hours, for about 2 hours to about 6 hours, or for about 2 hours to about 4 hours; e.g., the method comprises applying the contact lens to the eye for about 1, 2, 3, 4, 5, 6, 7, 8, 9, 10, 11, 12, 13, 14, 15, 16, 17, 18, 19, 20, 21, 22, 23, or 24 hours per day during the treatment period.

In certain embodiments, the treatment method comprises wearing the contact lens every day during the treatment period. In certain embodiments, the method comprises wearing the contact lens every other day (alternating) during the treatment period. In certain embodiments, the method comprises wearing the contact lens for night-time wear, e.g., while sleeping.

In certain embodiments, the one or more corneal softening agents are applied one or more times daily during the time the subject is wearing the contact lens. In certain embodiments, the one or more corneal softening agents are applied once, twice, three times, four times, or five times daily during the time the subject is wearing the contact lens. In other embodiments, the one or more corneal softening agents are applied every five minutes, every fifteen minutes, every half hour, every hour, every two hours, or every three hours during the time the subject is wearing the contact lens. The use of the one or more corneal softening agents is continued for as long as the subject wears the contact lenses. In certain embodiments, one corneal softening agent, or a combination of two or three different corneal softening agents are applied during the treatment period.

As generally described above, in certain embodiments, the one or more corneal softening agents are applied in combination with one or more therapeutic agents. In certain embodiments, the one or more therapeutic agents are applied once, twice, three times, four times, or five times daily during the time the subject is wearing the contact lens. In other embodiments, the one or more therapeutic agents are applied every five minutes, every fifteen minutes, every half hour, every hour, every two hours, or every three hours during the time the subject is wearing the contact lens. The use of the one or more therapeutic agents is continued for as long as the subject wears the contact lenses. In certain embodiments, one therapeutic agent, or a combination of two or three different therapeutic agents are applied during the treatment period. In certain embodiments, the one or more therapeutic agents are applied to the eye at the same time schedule as the one or more corneal softening agents, or are applied on a different time schedule.

In certain embodiments, the one or more corneal softening agents are impregnated or coated on the contact lens to allow for time-release (e.g., continuous delivery) of the agent to the eye, and thus the additional application of one or more corneal softening agents to the eye is then only optional.

In certain embodiments, the opthalmologic condition being treated is presbyopia, insufficient accommodation, or a condition associated with insufficient accommodation. Insufficient accommodation, also referred to as accommodative insufficiency (AI), involves the inability of the eye to focus property on an object. Visual accommodation is the process by which the eye increases optical power to maintain a clear image (focus) on an object as it draws near the eye. The pediatric subject's eye can change focus from distance to 7 cm from the eye in 350 milliseconds. This dramatic change in focal power of the eye of approximately 15 diopters (a diopter is 1 divided by the focal length in meters) occurs as a consequence of a reduction in zonular tension induced by ciliary muscle contraction. The amplitude of accommodation declines with age. By middle-age, the lens of the subject's eye loses its ability to focus, making it difficult to see objects up close. When this occurs, the subject is presbyopic. Once presbyopia occurs, those who are emmetropic (do not require optical correction for distance vision) will need an optical aid for near vision; those who are myopic (nearsighted and require an optical correction for distance vision) will find that they see better at near without their distance correction; and those who are hyperopic (farsighted) will find that they may need a correction for both distance and near vision. The age-related decline in accommodation occurs almost universally, and by 60 years of age, most of the population will have noticed a decrease in their ability to focus on close objects. Exemplary symptoms of presbyopia and insufficient accommodation include but are not limited to decreased focusing ability for near objects (blurry near vision), asthenopia (eye strain), and headache. In certain embodiments, subjects with presbyopia or insufficient accommodation may opt for surgical treatments, such as scleral expansion bands, PresbyLASIK, or conductive keratoplasty, to correct the condition prior to use of the contact lens.

In certain embodiments, the opthalmologic condition being treated is induced myopia, also known as acquired myopia, in which a refractive shift toward myopia (e.g., induced shift towards near-sightedness) is caused and depends upon an initiating condition or agent. Exemplary conditions or agents which induce myopia include, but are not limited to, age related nuclear cataracts, exposure to pharmaceuticals such as sulfonamides, and a variability in blood sugar level. In certain embodiments, the methods described herein are directed to prevention of induced myopia.

In certain embodiments, the opthalmologic condition being treated is computer vision syndrome, or caused by computer vision syndrome. Computer vision syndrome (CVS) is a condition resulting from focusing the eyes on a computer display for protracted, uninterrupted periods of time. Exemplary symptoms of CVS include headache, blurred vision, neck pain, redness in the eyes, fatigue, asthenopia (eye strain), dry eyes, irritated eyes, double vision, polyopia, and decreased focusing ability (difficulty refocusing the eyes). These symptoms can be further aggravated by improper lighting conditions (e.g., glare- or bright overhead lighting) or air moving past the eyes (e.g. overhead vents, direct air from a fan).

In certain embodiments, the treatment method comprises inducing changes in the physiology and anatomy of the cornea. In certain embodiments, the method comprises changing the corneal power of the treated eye. In certain embodiments, the method comprises changing the radius of curvature of the anterior surface the eye. In certain embodiments, the treatment corrects the subjects' near vision, e.g., by 1, 2, 3, 4, or 5 Jaeger lines, e.g., as measured by the Jaeger test scale: J1, J2=Font size 4 (fine print); J2, J3=Font size 5 (stocks); J4/J5=Font size 6 (yellow pages); J6=Font size 8 (Newspaper); J8=Font size 10 (Adult books); J9-J11=Font size 14 (Children's books); J11, J12=Font size 18 (Large print)). In certain embodiments, the method corrects the subjects' near vision without diminishing substantially far vision. In certain embodiments, the method corrects the subjects' near vision without diminishing far vision. In certain embodiments, the method corrects the subjects' far vision. In certain embodiments, the method corrects both near vision and far vision of the treated subject.

In certain embodiments, in any of the above described methods, the treatment method is the first-line treatment. However, in other embodiments, the subject may have already undergone surgery to correct a refractive error of an eye (e.g., by surgically changing the curvature of the cornea) and the method may be used to correct any remaining refractive error after surgery. In certain embodiments, the method allows for correction of any remaining refractive error of the eye without additional surgery. Exemplary surgical eye treatments include, but are not limited to, keratotomy, keratomileusis by a freezing process, automated lamellar keratomileusis (ALK), photo-reactive keratomileusis (PRK), laser-assisted in situ keratomileusis (LASIK), laser intrastromal keratomileusis, laser epithelial keratomileusis (LASEK), conductive keratoplasty (CK), and scleral resection. See, for example, US Patent Application Publication No. 2003/0139737 and U.S. Pat. Nos. 5,144, 630; 5,520,679; 5,484,432; 5,489,299; 5,722,952; 5,465, 737; 5,354,331; 5,529,076, 6,258,082; and 6,263,879.

Pharmaceutical Compositions

As generally described herein, in certain aspects, provided is a method for treating an ophthalmologic condition, the method comprising applying a contact lens and one or more corneal softening agents, and optionally one or more therapeutic agents, to the eye of a subject suffering from or likely to suffer from an ophthalmologic condition, as described herein. The one or more corneal softening agents and optionally one or more therapeutic agents ("agents") may be provided in the same pharmaceutical composition or separate pharmaceutical compositions. The pharmaceutical composition is a composition suitable for ocular administration, and comprises, in addition to the one or more agents, one or more pharmaceutically acceptable excipients.

In certain embodiments, the pharmaceutical composition comprises one agent and a pharmaceutically acceptable excipient. In certain embodiments, the pharmaceutical composition comprises two agents and a pharmaceutically acceptable excipient. In certain embodiments, the pharmaceutical composition comprises more than two agents and a pharmaceutically acceptable excipient. In certain embodiments, where two or more agents are administered, the agents may be provided in the same pharmaceutical composition or two or more separate pharmaceutical compositions.

Pharmaceutically acceptable excipients include any and all solvents, diluents or other liquid vehicles, dispersion or suspension aids, surface active reagents, isotonic reagents, thickening or emulsifying reagents, preservatives, solid binders, lubricants and the like, as suited to the particular dosage form desired. General considerations in formulation and/or manufacture of pharmaceutical compositions can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005). Certain excipients specifically contemplated for ocular administration include, but are not limited to, (tridistilled) water, saline, buffering agents, salts, lubricants (e.g., oily liquid carriers), and other viscosity-enhancing vehicles useful for prolonging of the period of contact of the agent to the eye, such as hydrogels, mucoadhesive substances, and polymers (e.g., hydrophobic and hydrophilic polymers). Exemplary polymers contemplated for use with the present method include, but are not limited to, cellulose, methylcellulose, polyvinylalcohol, and polyethylene glycol.

Relative amounts of the one or more agents, the pharmaceutically acceptable excipient, and/or any additional ingredients in a pharmaceutical composition will vary, depending upon the identity, size, and/or condition of the subject treated and further depending upon the route by which the composition is to be administered. In certain embodiments, the method contemplates non-invasive (topical) administration, such as administering the pharmaceutical composition formulated as a liquid (eye-drops, spray) or gel (e.g., semi-solid gel) to the eye of the subject. In other embodiments, the method contemplates injecting a pharmaceutical composition into the eye, e.g., the cornea of the eye, and in this instance, the pharmaceutical composition is formulated as an injectable liquid. In certain embodiments, the liquid or gel pharmaceutical composition is hypertonic (5% to 40%, e.g., 10, 20, 30, or 40%) or hypotonic (0% to 5%, e.g., 1, 2, 3, or 4%) depending on the needs of the subject (e.g., such as working needs, rest hours, sleeping).

In certain embodiments, a kit is provided comprising the pharmaceutical composition comprising one or more agents (e.g., corneal softening agents, therapeutic agents). The kit may optionally further include contact lenses, lubricating eye-drops, cleaning solutions for the contact lenses, a contact lens carrying case, an extra pair of contact lenses, and instructions for wearing the contact lenses.

Corneal Softening Agents

As generally described herein, in certain aspects, provided is a method for treating an ophthalmologic condition, the method comprising applying a contact lens and one or more corneal softening agents to the eye of a subject suffering from or likely to suffer from an ophthalmologic condition, e.g., applying 1, 2, 3, 4, 5, 6, 7, 8, 9, or 10 different corneal softening agents to the eye. Such a method may further comprise applying one or more corneal softening agents in combination with one or more therapeutic agents to the eye.

"Corneal softening agents" are agents which break down various structural components of the cornea, thereby softening the cornea and allowing the contact lens to mold the cornea to the desired shape. Such agents include, but are not limited to, exogenous enzymes and agents useful in activating endogenous enzymes of the eye.

The structural components of the human cornea are chiefly proteoglycans and collagens. Proteoglycans are composed of a hyaluronate core, a protein core, and glycosaminoglycans, which are proteoglycan monomers with repeating disaccharide units. Approximately 60% of the glycosaminoglycans of the cornea are made up of keratin sulfate, while the remaining 40% are mostly chondroitin sulfate. The other main structural component of the cornea, collagen, is found in seven different forms in the human cornea. Exemplary exogenous enzymatic corneal softening agents which are contemplated useful in combination with the lenses include, but are not limited to, hyaluronidase, chondroitinase ABC, chondroitinase AC, endo B-galactosidase (keratanase), stromelysin (MM3), bacterial collagenase, interstitial collagenase (MM1), and gelatinase (MM2). Exemplary agents useful in activating endogenous enzymes, such as endogenous metalloproteinases, of the eye include, but are not limited to, interleukin-la, tumor necrosis factor, monosodium urate monohydrate, 4-amino phenylmercuric acetate, human serum amyloid A, human $B_2$ microglobin, and copper chloride. See, e.g., U.S. Pat. Nos. 5,626,865 and 6,132,735. Other corneal softening agents include carbamide. Other enzymes that degrade other sugars or proteins found in the cornea may also be used in combination with the contact lens. In certain embodiments, the enzymes act to level the unions of the lamellas in the cornea. In other embodiments, an agent known to change the sustentation forces of the molecular structure of the cornea (e.g., corneal lamellas) is used in combination with the contact lens.

In certain embodiments, the method comprises applying the enzyme hyaluronidase to the eye in combination with the contact lens. Hyaluronidase is an enzyme that degraded mucopolysaccharides by catalyzing the hydrolysis of the one to four linkages in hyaluronic acid, chondroitin, and chondroitin 4 sulfates A & C. Mucopolysaccharide is one of the intracellular ground substances (cement or glue) of the stroma, the connective-type tissue of the middle layer of the cornea. The shape of the cornea is largely dependent on the arrangement of collagen fibrils in the stromal layers of the cornea and on the arrangement of the mucopolysaccharides layers between these fibrils. Hyaluronidase breaks down the mucopolysaccharide chains when released into the cornea. The stroma of the cornea is thereby softened making it more amenable to reshaping by the contact lens.

Hyaluronidase may be obtained from a variety of natural sources from which the enzyme can be purified to at least 90% purity, at least 95% purity, at least 96% purity, at least 97% purity, at least 98% purity, or at least 99% purity. Natural sources include bovine (bull) testes, ovine (sheep) testes, leeches, and bacteria (*Streptomyces*). In certain embodiments, hyaluronidase is commercially available. For example, one form of hyalouronidase is available under the trade name WYDASE® (Wyeth Laboratories, Inc., Philadelphia, Pa.). The WYDASE® hyaluronidase is a preparation of highly purified bovine testicular hyaluronidase. The hyaluronidase enzyme may be supplied as a lyophilized powder. The powder can be reconstituted using phosphate buffer-saline solution. Typical proportions include approximately 150 USP units of hyaluronidase per 1 milliliter. In certain embodiments, the hyaluronidase is prepared using recombinant DNA technology. The hyaluronidase may be a modified version, e.g., a cleaved form, chemically modified, or genetically modified. In certain embodiments, the concentration (weight percent) of hyaluronidase in the pharmaceutical composition ranges from 0.01% to 10%, or 0.1% to 8%, or 0.1% to 7%, or 0.1% to 6%, or 0.1% to 5%, or 1% to 6% weight percent. In certain embodiments, the concentration is about 1 to about 10 USP units per mL, e.g., about 1, 2, 3, 4, 5, 6, 7, 8, 9, or 10 USP units per mL. In certain embodiments, the concentration is about 3 to about 8 USP units per mL, about 4 to about 7 USP units per mL, or about 5 to about 6 USP units per mL of hyaluronidase.

In certain embodiments, the method comprises applying a bacterial collagenase (e.g., a *Clostridium* collagenase) to the eye in combination with the contact lens. In certain embodiments, the bacterial collagenase is a collagenase secreted by the bacteria *Clostridium histolyticum*. In certain embodiments, the bacterial collagenase is prepared using recombinant DNA technology. In other embodiments, the bacterial collagenase is purified from a natural source. The bacterial collagenase may be a modified version, e.g., a cleaved form, chemically modified, or genetically modified. In certain embodiments, the concentration (weight percent) of bacterial collagenase in the pharmaceutical composition ranges from 0.01% to 10%, or 0.1% to 8%, or 0.1% to 7%, or 0.1% to 6%, or 0.1% to 5%, or 1% to 6% weight percent. In certain embodiments, the concentration is about 5 to about 15 USP units per mL, e.g., about 5, 6, 7, 8, 9, 10, 11, 12, 13, 14, or 15 USP units per mL. In certain embodiments, the concentration is about 8 to about 15 USP units per mL, about 10 to about 15 USP units per mL, or about 10 to about 12 USP units per mL of bacterial collagenase.

In certain embodiments, the method comprises applying hyaluronidase and bacterial collagenase to the eye in combination with the contact lens. In certain embodiments, the method comprises applying about 0.1% to about 10% hyaluronidase and about 0.1% to about 10% bacterial collagenase to the eye in combination with the contact lens. In certain embodiments, the method comprises applying about 1 to about 10 USP units per mL hyaluronidase and about 5 to about 15 USP units per mL bacterial collagenase to the eye in combination with the contact lens.

In other embodiments, the method comprises applying other combinations of hyaluronidase and another corneal softening agent to the eye in combination with the contact lens. For example, in certain embodiments, the method comprises applying hyaluronidase and interstitial collagenase (MM1) to the eye in combination with the contact lens. In certain embodiments, the method comprises applying a hyaluronidase and gelatinase (MM2) to the eye in combination with the contact lens.

Therapeutic Agents

As generally described herein, in certain aspects, provided is a method for treating an ophthalmologic condition, the method comprising applying a contact lens and a combination of one or more corneal softening agents and one or more therapeutic agents to the eye of a subject suffering from or likely to suffer from an ophthalmologic condition, e.g., one or more corneal softening agents in combination with 1, 2, 3, 4, 5, 6, 7, 8, 9, or 10 different therapeutic agents to the eye. Various therapeutic agents are contemplated improve therapy, such as, for example, by reducing inflammation, reducing irritation, improving comfort of the subject, reducing the chance of infection, and improving the activity of the corneal softening agents, such as by reducing wound healing and/or reducing the regression back to the pre-treatment condition. Exemplary therapeutic agents include, but are not limited to, anesthetics, vitamins, zinc, antibiotics, anti-allergic agents, cytokinases, vasoconstrictors, anti-viral agents, anti-fungal agents, anti-inflammatory agents, and lubricants.

In certain embodiments, the method comprises applying an anesthetic used to reduce the irritation of the contact lens on the cornea in combination with the contact lens and one or more corneal softening agents. Examples of anesthetics include benzocaine, bupivacaine, cocaine, etidocaine, lidocaine, mepivacaine, pramoxine, prilocaine, chloroprocaine, procaine, proparacaine, ropicaine, and tetracaine.

In other embodiments, the method comprises applying an anti-inflammatory agent, such as a steroid or a non-steroidal anti-inflammatory agent, in combination with the contact lens and one or more corneal softening agents. Example of anti-inflammatory agents include aspirin, acetaminophen, indomethacin, sulfasalazine, olsalazine, sodium salicylate, choline magnesium trisalicylate, salsalate, diflunisal, salicylsalicylic acid, sulindac, etodolac, tolmetin, diclofenac, ketorolac, ibuprofen, naproxen, flurbiprofen, ketoprofen, fenoprofen, suprofen, oxaproxin, mefenamic acid, meclofenamic acid, oxicams, piroxicam, tenoxicam, pyrazolidinediones, phenylbutazone, oxyphenthatrazone, pheniramine, antazoline, nabumetone, COX-2 inhibitors (Celebrex), apazone, nimesulide, and zileuton. Glucocorticoids such as hydrocortisone, prednisolone, fluorometholone, and dexamethasone may also be used as anti-inflammatory agents.

In still other embodiments, the method comprises applying a lubricant in combination with the contact lens and one or more corneal softening agents. These agents are included to improve the comfort of the subject during the treatment. One of skill in this art based on the individual subject determines the composition of the eye drops being prescribed for the subject.

In certain other embodiments, the method comprises applying anti-microbial agents, such as anti-bacterial, anti-viral, and/or anti-fungal agents, in combination with the contact lens and one or more corneal softening agents. Exemplary anti-microbial agents include bacitracin zinc, chloramphenicol, chlorotetracycline, ciprofloxacin, erythromycin, gentamicin, norfloxacin, sulfacetamide, sulfisoxazole, polymyxin B, tetracycline, tobramycin, idoxuridine, trifluridine, vidarabine, acyclovir, foscarnet, ganciclovir, natamycin, amphotericin B, clotrimazole, econazole, fluconazole, ketoconazole, miconazole, flucytosine, clindamycin, pyrimethamine, folinic acid, sulfadiazine, and trimethoprim-sulfamethoxazole.

In certain other embodiments, the method comprises applying vasoconstrictors in combination with the contact lens and one or more corneal softening agents. Vasoconstrictors may include dipivefrin (propine), epinephrine, phenylephrine, apraclonidine, cocaine, hydroxyamphetamine, naphazoline, tetraliydrozoline, dapiprazole, betaxolol, carteolol, levobunolol, metipranolol, and timolol.

In certain other embodiments, the method comprises applying vitamins or other nutrients such as vitamin A, vitamin $B_{15}$ vitamin $B_6$, vitamin $B_{12}$, vitamin C (ascorbic acid), vitamin E, vitamin K, and zinc in combination with the contact lens and one or more corneal softening agents.

An exemplary pharmaceutical composition for use with the contact lenses includes applying a pharmaceutical composition comprising a combination of hyaluronidase and bacterial collagenase to the eye, and optionally may additionally include applying one or more of the following: 5-10% anesthetic, 10-20% antibiotic, 10-20% anti-inflammatory agent, 20-30% anti-allergic agent, 20-30% vitamin A, 3-5% carbamide (urea), 2-5% cytokinase, 10-20% vasoconstrictor, and/or a 1-30% of one or more viscosity enhancing vehicles, to the eye.

EXAMPLES

The following examples are intended to illustrate certain embodiments of the invention described herein, and are not to be construed as limiting and do not exemplify the full scope of the invention.

Example 1: Contact Lens for Use in the Correction of Presbyopia

The procedure for determining a proper fit for the contact lens utilizes topographical maps for K readings (corneal curvature) and eccentricity. The goal in this example was to have the steepest possible lens on the eye that does not create an air bubble. The lens was also required to center well and move 0.5 to 1.0 mm or less on each blink. Overrefraction was used to determine the proper lens power.

Figures 4A, 4B:
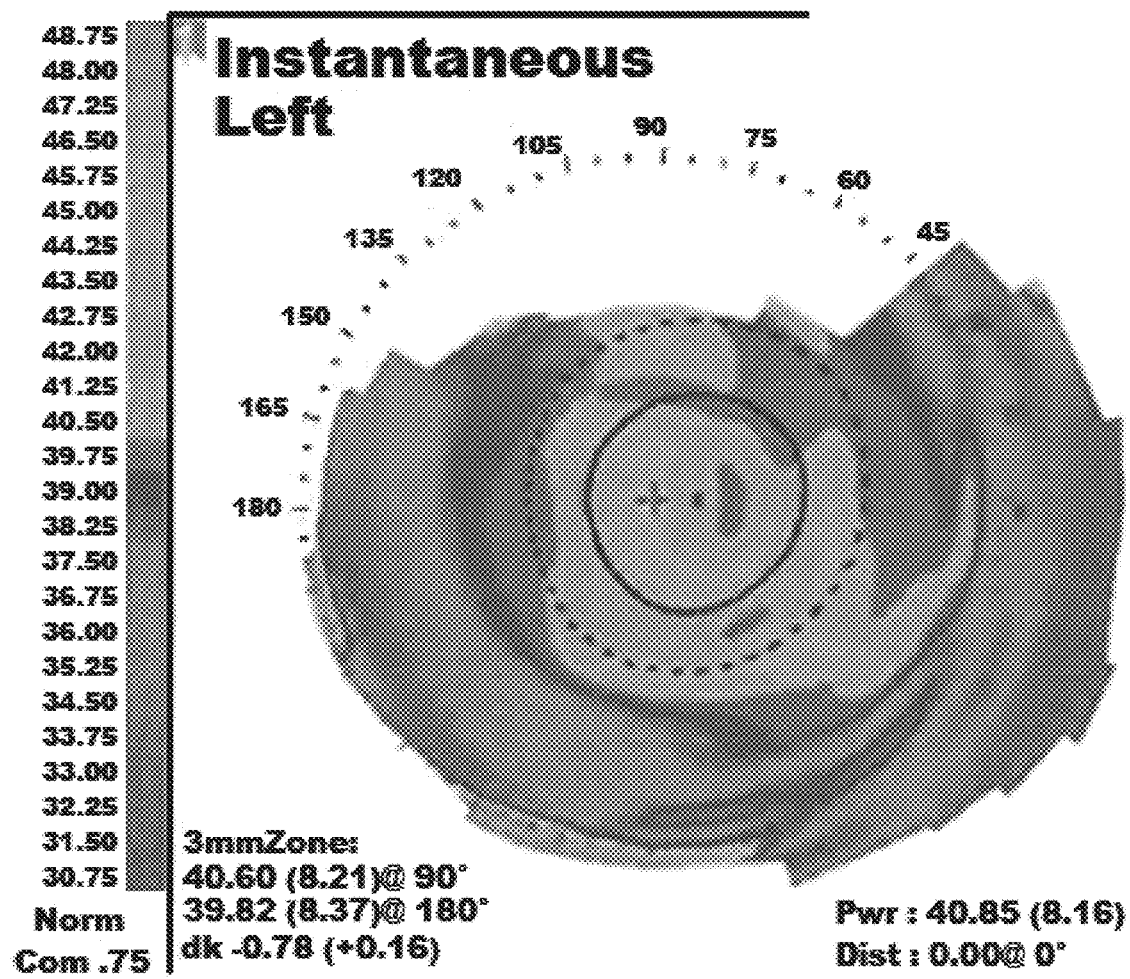
FIG. 4A is an instantaneous tangential map of an eye taken for diagnostic purposes.
FIG. 4B is a standard refractive map used to fit a contact lens.

FIG. 4A depicts an Instantaneous (tangential) map (left) with SimK's—40.60 @ 90 degrees and 39.82 @ 180 degrees. FIG. 4B shows a Standard 2 (Refractive left) map with an Eccentricity (Asphericity) of 0.22.

The Diagnostic Lens had the following parameters:

| Base curve | Power | Diameter | Over-refraction |
|---|---|---|---|
| 45.00 D | −5.50 D | 9.6 mm | +1.25 D |

Figure 4C:
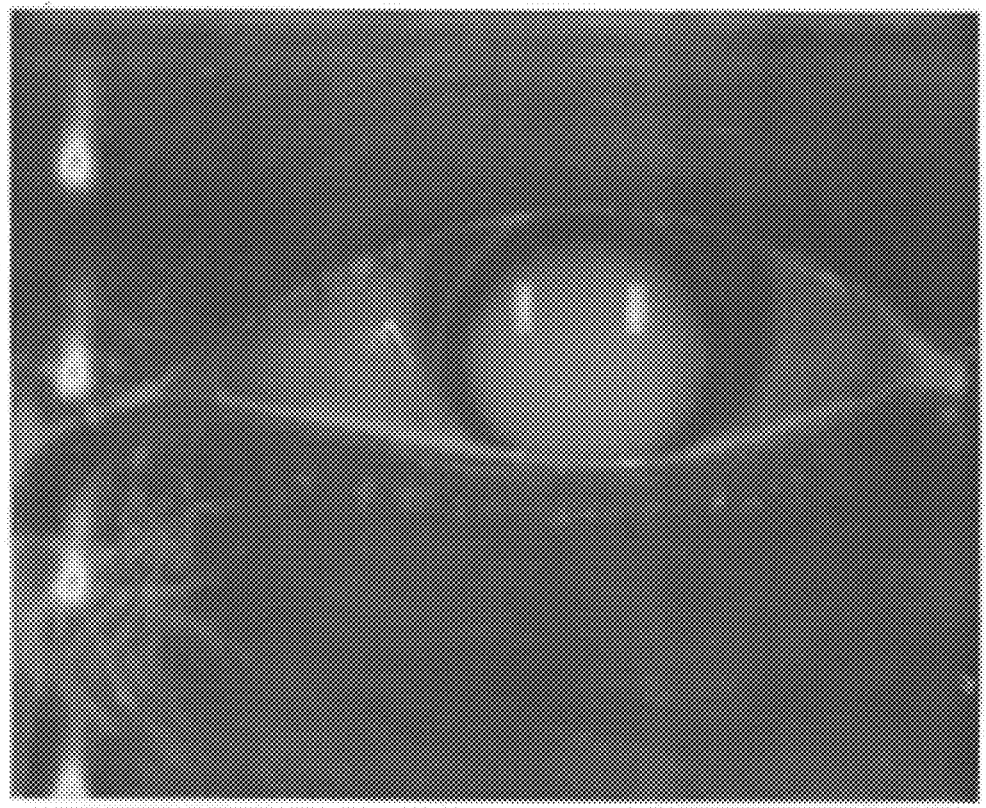
FIG. 4C is a fluorescein pattern showing lens clearance.

FIG. 4C depicts a fluorescein pattern showing lens clearance using fluorescein and black light.

Based on the fit assessed using the Diagnostic Lens and the determined over-refraction, the Selected Lens ordered had the following parameters:

| Base Curve | Power | Diameter | Optic Zone |
|---|---|---|---|
| 45.00 D | −4.25 D | 9.6 mm | 8.0 mm |

The secondary peripheral curve, which corresponds to the inner peripheral region of FIGS. 2A and 2C, had a radius of curvature of 8.00 mm and had a width of 0.4 mm. The peripheral curve, which corresponds to the outer peripheral region of FIGS. 2A and 2C, had a radius of curvature of 11.00 mm and had a width of 0.4 mm.

Example 2: Correction of Presbyopia in a Patient Population

Figure 5B:
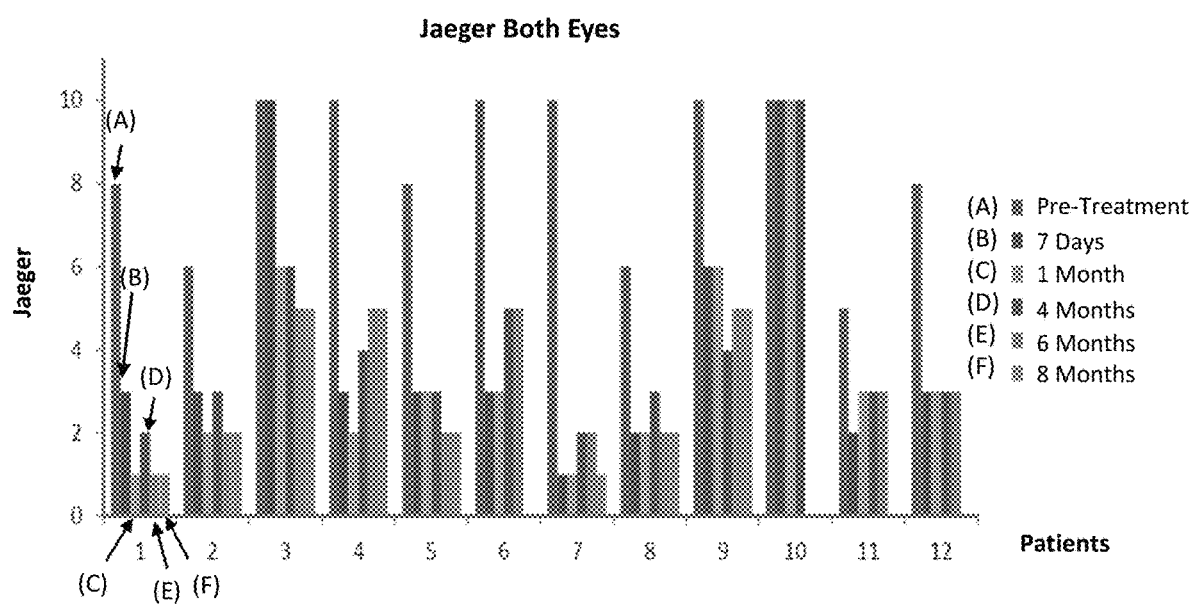

FIGS. 5A and 5B provide data from a 12-patient sample of a clinical study within a presbyopic population in Mexico using a contact lens and an enzymatic formulation comprising hyaluronidase and bacterial collagenase. In this study, the presbyopic patient is administered a formulation comprising hyaluronidase and bacterial collagenase to the eye in combination with a contact lens of the present invention. The treatment period is typically four to eight hours per day for about four to seven days. Pre-treatment measurements and measurements seven days, fourteen days, one month, four months, six-months, and eight months post-treatment for both near and far vision are recorded by the optometrist.

With the exception of one patient (patient 10), each patient's near vision acuity in this 12-patient sample improved after treatment, and this improvement lasted for at least eight months post-treatment. Furthermore, unlike other methods for treating presbyopia, the treatment did not result in improved near vision at the expense of the patient's far vision. On the contrary, the patient's far vision remained undiminished after treatment, and most remarkably, the majority experienced improved far vision which lasted at least six months post-treatment; see, e.g., results for patients (1) to (5) and (7) to (9), (11) and (12) at six months, and results for patients (1) to (5) and (7) to (9) at eight months. Patients (6), (11), and (12) did not participate in the eight month measurement. Patient (10) did not participate in the six and eight month measurements, and has since dropped out of the study.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

Having thus described several aspects of at least one embodiment of this invention, it is to be appreciated various alterations, modifications, and improvements will readily occur to those skilled in the art. Such alterations, modification, and improvements are intended to be part of this disclosure, and are intended to be within the spirit and scope of the invention. Accordingly, the foregoing description and drawings are by way of example only.

What is claimed is:

1. A method of using a contact lens, comprising:
   placing a contact lens on a cornea of an eye such that, when the contact lens is fit on to the eye, a fluid volume between the cornea of the eye and the contact lens is maintained between 0.05 cubic mm and 0.3 cubic mm, the contact lens comprising:
   an optic zone having an optic zone diameter of between 7.0 mm and 9.0 mm and a radius of curvature of between 7.0 mm and 10.0 mm, wherein the optic zone has a curvature that varies from a curvature at the flattest corneal meridian of the eye by between 2.0 and 6.0 diopters; and
   an inner peripheral region surrounding the optic zone, wherein the inner peripheral region has a radius of curvature of between 0.5 mm and 1.5 mm greater than a radius of curvature of the optic zone.

2. A method for treating an ophthalmologic condition, the method comprising using the contact lens according to claim 1 and applying one or more corneal softening agents to the eye of a subject suffering from or likely to suffer from the ophthalmologic condition.

3. The method of claim 2, wherein the condition is presbyopia, computer vision syndrome (CVS), or insufficient accommodation.

4. The method of claim 2, wherein the one or more corneal softening agents is selected from the group consisting of hyaluronidase, chondroitinase ABC, chondroitinase AC, endo B-galactosidase (keratanase), stromelysin (MM3), bacterial collagenase, interstitial collagenase (MM1), and gelatinase (MM2).

5. The method of claim 4, wherein the method comprises applying hyaluronidase and bacterial collagenase to the eye.

6. The method of claim 5, wherein the method comprises applying 1 to 10 USP units per mL hyaluronidase and about 5 to about 15 USP units per mL bacterial collagenase to the eye.

7. The method of claim 1, wherein the optic zone includes a curvature that is greater than a curvature at the flattest corneal meridian of the eye by between 2.0 and 6.0 diopters.

8. The method of claim 1, wherein the optic zone includes a curvature that is less than a curvature at the flattest corneal meridian of the eye by between 2.0 and 6.0 diopters.

9. The method of claim 1, wherein the optic zone includes a curvature that varies from a curvature at the flattest corneal meridian of the eye by between 3.5 and 5.5 diopters.

10. The method of claim 1, wherein the fluid volume between the cornea of the eye and the contact lens is a tear volume.

11. The method of claim 1, wherein, when the contact lens is fit on to the eye, upon blinking of the eye, the contact lens does not move by more than 1 mm.

12. The method of claim 1, wherein, when the contact lens is fit on to the eye, bubbles greater than 0.5 mm in diameter are prevented from forming between the contact lens and the eye.

13. The method of claim 1, wherein the inner peripheral region is adjacent to the optic zone.

* * * * *